United States Patent [19]

Evans et al.

[11] Patent Number: 5,593,678
[45] Date of Patent: Jan. 14, 1997

[54] PROTECTION OF TELEOST FISH

[75] Inventors: Donald L. Evans; Liliana Jaso-Friedmann, both of Athens, Ga.

[73] Assignee: University of Georgia Research Foundation, Athens, Ga.

[21] Appl. No.: 321,231

[22] Filed: Oct. 11, 1994

[51] Int. Cl.$^6$ .................. A61K 39/00; A01N 59/26; C01B 7/00

[52] U.S. Cl. .................. 424/184.1; 424/606; 424/646; 424/665; 423/462

[58] Field of Search .................. 424/184.1, 606, 424/646, 665; 423/462

[56] References Cited

PUBLICATIONS

Evans, D. L. and Jaso–Friedmann, L. (1994) "Role of Protein Phosphatases in the Regulation of Nonspecific Cytotoxic Cell Activity," *Developmental and Comparative Immunology*, 2 (vol. 18):137–146.

Jaso–Friedmann, L. et al. (1994) "Pathways of Signaling in Nonspecific Cytotoxic Cells: Effects of Protein Kinase and Phosphatase Inhibitors and Evidence for Membrane Tyrosine Phosphorylation," *Cellular Immunology*, 1(vol. 153):142.

Evans, D. L. et al. (1990) "Pathways of Signal Transduction in Teleost Nonspecific Cytotoxic Cells," *Developmental and Comparative Immunology*, 14:295–304.

Jaso–Friedmann, L. et al. (1993) "Nonspecific Cytotoxic Cells in Fish: Antigens Cross–Reactivity of a Function Associated Molecule with the Intermediate Filament Vimentin," *Cellular Immunology*, 148:208–217.

Evans, D. L. et al. (1993) "Identification of a Vimentin–Like Function Associated Molecule (FAM) on Rat NK Cells: Evidence for Receptor Function," *Scand. J. Immunol.*, 37:131–142.

Graves, S. S. et al. (Jan. 1985) "Antiprotozoan Activity of Nonspecific Cytotoxic Cells (NCC) from the Channel Catfish (*Ictalurus Punctatus*)", *The Journal of Immunology*, 1(vol. 134):78–85.

Alexander, D. R. (Dec. 1990), "The Role of Phosphatases in Signal Transduction," *The New Biologist*, 12(vol. 2):1049–1062.

Fischer, E. H. et al, (Jul. 26, 1991) "Protein Tyrosine Phosphatases: A Diverse Family of Intracellular and Transmembrane Enzymes," *Articles*, pp. 401–406.

Verma et al. 1988 Ad. Bios. 7(1):73–78.

Sargent et al. 1980, Comp. Biochem. Physiol. 66C:111–114.

Bertolini et al. 1990, J. Wildlife Dis. 26(2) 246–252.

Ewing et al. 1992, Parasitology Today 8(6):204–208.

Hilton et al. 1988, Aquatic Toxicology. 12:63–71.

*Primary Examiner*—James C. Housel
*Assistant Examiner*—Jennifer Shaver
*Attorney, Agent, or Firm*—Greenlee, Winner and Sullivan, P.C.

[57] ABSTRACT

Utility of protein phosphatase inhibitors to protect teleost fish from microorganismic pathogens is disclosed. The present invention provides pharmaceutical compositions, kits, and methods of therapeutic and prophylactic treatments comprising sodium orthovanadate or vanadate-mimetic protein phosphatase inhibitors to protect fish, for example, catfish, from infection and disease caused by microorganismic pathogens, e.g., Edwardsiella. Sodium orthovanadate, a protein phosphatase inhibitor, and vanadate-mimetic protein phosphatase inhibitors activate in vitro and in vivo the cytotoxicity of teleost nonspecific cytotoxic cells (NCC).

18 Claims, 11 Drawing Sheets

PROTECTION OF TELEOST FISH

This invention was made with partial support of the United States government. The United States government has certain rights in this invention.

1. Field of the Invention

This invention relates to the protection of teleost fish against microorganismic pathogens. Sodium orthovanadate, a protein phosphatase inhibitor, or a vanadate-mimetic protein phosphatase inhibitor is used to protect fish therapeutically or prophylactically from infection or disease caused by microorganismic pathogens.

2. Background of the Invention

Nonspecific cytotoxic cells (NCC) from teleost fish are believed to be comparable to mammalian natural killer (NK) cells. NCC lyse a wide variety of mammalian transformed tumor target cells and may participate as major effector cells in killing protozoan parasites. Compared to all known effector functions of specific and nonspecific immunity in fish, NCC may represent the most broadly functional defense against infectious agents as well as participating in immunoregulation.

NCC and NK cells share many characteristics, some of which are: lack of restriction for target cell recognition by MHC or H2 antigens, inability to produce secondary responses, and ability to lyse tumor and virus transformed target cells and various parasitic protozoans. The differences between NCC, mouse, and human NK cells provide perhaps the most significant information regarding the evolution of NK/NCC cells as well as providing clues regarding their roles in natural immune responses. For example, NCC are small agranular lymphocytes (SAL) [Evans et al. (1987) *Dev. Comp. Immunol.* 11:95], and chickens and pigs have SAL [Sieminski-Brodzina et al. (1991) *Dev. Comp. Immunol.* 15:181], and large granular lymphocytes (LGL) [Takamatsu et al. (1985) *Jpn. J. Vet. Sci.* 47:749], while mice, rats, and humans have LGL. Fresh NCC, unlike similarly prepared murine and human NK cells, have a wide range of target cell specificities [Graves et al. (1984) *Dev. Comp. Immunol.* 8:293; Evans et al. (1984) *Dev. Comp. Immunol.* 8:303] like mammalian LAK and ALAK [Jaso-Friedmann et al. (1993) *J. Natl Immun.* 12:316–325]. These comparisons provide some evidence for phylogenetic equivalencies.

Recently, a receptor-like molecule on NCC and NK cells was isolated by the inventors from many different species [Evans et al. (1988) *J. Immunol.* 141:324; Harris et al. (1991) *Proc. Natl. Acad. Sci.* 88:3006; Jaso-Friedmann et al. (1992) *Cell Immunol.* 141:293]; this work provides the best evidence yet for an evolutionary relationship. The expression of this protein on NK cells from diverse species closely links natural immune mechanisms of target cell recognition.

Monoclonal antibodies (mab) specific for the putative receptor (e.g., mab 5C6) inhibited cytotoxicity of NCC and NK cells [Evans et al. (1988) supra, Harris et al. (1991) supra, Jaso-Friedmann et al. (1992) Supra]. The mab 5C6 binding to NCC and NK cells also triggered many different levels of activation responses [Evans et al. (1990a) *Dev. Comp. Immunol.* 14:223; Evans et al. (1990b) *Dev. Comp. Immunol.* 14:295; Evans et al. (1990c) *Nat. Immun. Cell Growth Regul.* 9:353–365; Evans et al. (1992) *Dev. Comp. Immunol.* 16:383]. NCC and NK cells appeared to have some equivalent second messenger responses, whereas in other important comparative areas of signaling, agonist binding appeared to initiate additional requirements for NCC activation. These included an increased dependence on intracellular calcium levels for activation and lack of synergistic requirements for costimuli effects to trigger lytic responses. For example, calcium appeared to participate in more direct pathways of signaling in NCC compared to NK cells [Evans et al. (1990a) supra, Evans et al. (1990b) supra, Evans et al. (1992) supra]. The calcium ionophore A23187 in the absence of PMA or mab 5C6 activated NCC cytotoxicity and increased "receptor" expression.

There appears to be general agreement [Jaso-Friedmann et al. (1993) *Cell Immunol.* 148:208; Evans et al. (1990) *Dev. Comp. Immunol.* 14:223; Evans et al. (1990) *Dev. Comp. Immunol.* 14:295; Evans et al. (1992) supra; and Stahls et al. (1992) *Eur. J. Immunol.* 22:611] that both-kinases and phosphatases regulate some signaling pathways. The prototype protein phosphatase which provides the best evidence for the role of these enzymes in signaling responses in lymphocytes is the CD45 glycoprotein. CD45 is expressed on all (human) lymphocytes, and it belongs to the "receptor-type" phosphotyrosyl-protein phosphatase (PTPase) family of enzymes (including LAR-leukocyte antigen related and leukocyte common antigen-related phosphatase-LRP). Inclusion of these proteins in this family is based on amino acid sequence homology [Fischer et al. (1991) *Science* 253:401; Alexander et al. (1990) *The New Biologist* 2:1049] with a PTPase purified from human placental tissue (i.e., PTB1B). Within this group of membrane and cytosolic enzymes, all share significant conserved cytoplasmic domain sequences (707 amino acids). More than 90% of the cytoplasmic portion of CD45 of mouse, rat and humans is identical [Evans et al. (1988) supra]. The extracellular regions of protein phosphatase generally are composed of several immunoglobulin-like and fibronectin type-III-like domains [Alexander et al. (1990) supra; Krueger et al. (1990) *EMBO J.* 9:3241] and they are markedly heterogenic in sequence and size (i.e., vary from 27–1599 amino acids). Although a sequence motif is common to many of the extracellular portions of protein phosphatases, there is not enough sequence homology between any of the protein phosphatases in the extracellular region to suggest that they have common substrates to which they bind. The nonreceptor-type protein phosphatases lack extracellular and transmembrane domains and have a significantly different structure compared to the receptor-type protein phosphatases [Graves et al. (1984) supra; Schechter et al. (1980) *Nature* 284:556].

There is considerable information to suggest that CD45 may be involved in T-cell signaling responses. Crosslinking CD45 with CD3 or with CD2 affects T-cell activation [Tamura et al. (1984) *J. Biol. Chem.* 259:6650; Gil et al. (1988) *J. Biol. Chem.* 263:1868; Fantus et al. (1990) *Endocrin.* 127:2716; Earp et al. (1983) FEBS Lett. 161:180; Ledbetter et al. (1988) *Proc. Natl. Acad. Sci.* 85:8628]. Crosslinkage of CD45 with CD4 induces intracellular calcium release. The possible functional as well as physical association between these molecules suggested that the CD45 protein phosphatase plays a role in T-cell activation responses. Additional evidence that CD45 participates in T-cell signaling was shown in studies where CD45 deficient (mutant) cell lines failed to produce phosphatidylinositol metabolites following stimulation [Kiener et al. (1989) *J. Immunol.* 143:23; Shaw et al. (1991) *Curr. Opin. Cell Biol.* 3:862].

Although the substrates recognized by many of the protein phosphatases have not yet been detected, a likely candidate for the CD45 phosphatase is $p56^{lck}$. This cytoplasmic kinase is a member of the src oncogene family of kinases [Livanainen et al. (1990) *Eur. J. Immunol.* 20:2509] and in T-cells is biochemically and physically associated with the cytoplasmic domains of CD4 and CD8 [Odum et al.

(1991) *Human Immunol.* 32:85]. P56$^{1ck}$ is probably activated (regulated) by dephosphorylation of Tyr$^{505}$ by CD45. Following this activation step, P56$^{1ck}$ autophosphorylates and initiates its action on the zeta chain [Mustelin et al. (1989) *Proc. Natl. Acad. Sci.* 86:6302].

SUMMARY OF THE INVENTION

The present invention provides a protein phosphatase inhibitor, immediately exemplified as sodium orthovanadate (vanadate), that functions to protect fish from microorganismic pathogens. The subject invention also uses a vanadate-mimetic protein phosphatase inhibitor, i.e., a protein phosphatase inhibitor that mimics or simulates a biological action or effect of sodium orthovanadate, to protect teleost fish from infections caused by microorganismic pathogens.

In specific embodiments of this invention, sodium orthovanadate, a protein phosphatase inhibitor, was used therapeutically to treat catfish preinfected with amounts of *Edwardsiella ictaluri* sufficient to produce 100% mortality such that mortality was reduced and the orthovanadate-treated fish were protected against the development or progression of diseases associated with the Edwardsiella pathogen. This invention further contemplates the use of vanadate-mimetic protein phosphatase inhibitors to treat therapeutically fish that are infected with a microorganismic pathogen in order to protect the infected fish against the development and progression of diseases associated with the pathogen.

Other embodiments of this invention disclose a prophylactic use of sodium orthovanadate to protect fish against infection with microorganismic pathogens to which the fish are normally susceptible. Catfish pretreated with sodium orthovanadate before exposure to amounts of *Edwardsiella ictaluri* sufficient to cause 100% mortality, produced resistance in catfish against the Edwardsiella pathogen. Thus, the orthovanadate prophylactic pretreatment protects fish against infection and disease caused by a microorganismic pathogen. This invention further contemplates the use of vanadate-mimetic protein phosphatase inhibitors to treat fish prophylactically to protect against infection and disease caused by a microorganismic pathogen.

The present invention also provides a method for the therapeutic or prophylactic treatment of fish with orthovanadate or a vanadate-mimetic protein phosphatase inhibitor against infection caused by a microorganismic pathogen. In specific embodiments of the invention, catfish infected with *Edwardsiella ictaluri* were treated with therapeutically effective concentrations, for example, between approximately 10 μM to approximately 25 μM, of a protein phosphatase inhibitor, for example, sodium orthovanadate, which conveyed protection on the infected fish against the development or progression of a disease associated with the pathogenic Edwardsiella. In other embodiments, catfish which were pretreated with prophylactically effective concentrations, for example, between approximately 5 μM to approximately 50 μM of a protein phosphatase inhibitor, for example, sodium orthovanadate, prior to exposure to a microorganismic pathogen, e.g., *Edwardsiella ictaluri* developed resistance to the pathogenicity of the Edwardsiella.

Significantly, the present invention provides a completely new approach for the production of resistance to microorganismic pathogens. This nonantigen specific and vaccine independent process for producing large populations of resistant catfish, provides a vehicle which does not rely on antibiotic therapy. Vanadate and vanadate-mimetic protein phosphatase inhibitors probably have a broad spectrum of activity against pathogens such as pathogenic bacteria, parasitic protozoans, viruses and fungi, among others. The useful applications of this mechanism of induction of nonspecific disease resistance include: (1) prophylactic prevention of disease outbreaks; (2) intervention and therapeutic treatment of infected fish; (3) treatment prior to anticipated stress conditions, i.e., changes in water quality including temperature, chemical contaminants, etc.; (4) pretreatment and treatment after shipping fish; (5) treatment of "sick" fish for home hobbyists; and (6) maintenance of health in fish for small and large scale, domestic and commercial growth and for scientific experiments. Reduction in losses from Edwardsiella infections in fingerling catfish alone could result in savings of millions of dollars annually for the commercial industry.

Siluriformes (catfish belong to this group) rank fifth internationally in annual production (approximately 250,000 tons) and continue to increase in importance as a source of food protein for human consumption. There are four main bacterial diseases of catfish which cause exorbitant and continuing economic losses in the commercial fish industry. These are *Edwardsiella ictaluri* (enteric septicemia), *Flexibacter columnaris*, *Aeromonas hydrophila*, and *Edwardsiella tarda*. Enteric septicemia is geographically widespread and is perhaps one of the most important pathogens of catfish. The present invention provides a treatment, e.g., with vanadate, that can (eventually) either be the sole regimen used, for example, to prevent or treat *Edwardsiella ictaluri* (enteric septicemia) disease outbreaks, or at the very minimum, be used in conjunction with antibiotic treatment or be used with specific vaccines.

This invention further provides a pharmaceutical composition, comprising sodium orthovanadate or a vanadate-mimetic protein phosphatase inhibitor and a pharmaceutical carrier suitable for teleost fish, that is useful for the therapeutic or prophylactic treatment of teleost fish against infection caused by a microorganismic pathogen. The pharmaceutical composition may further comprise an additional medicament in addition to the orthovanadate or vanadate-mimetic protein phosphatase inhibitor. For example, an antibiotic, a fungicide, a protein phosphatase inhibitor, an antiviral compound or an anti-inflammatory agent, among others, can be admixed into the pharmaceutical composition.

Also, this invention provides a commercially marketable kit comprising a pharmaceutical composition for the therapeutic or prophylactic treatment of a teleost fish against infection caused by a microorganismic pathogen. The pharmaceutical composition of the kit comprises an orthovanadate salt or a vanadate-mimetic protein phosphatase inhibitor and a pharmaceutical carrier acceptable to fish in a dispensable form (e.g., liquid, granular, tablet, etc.) such that a measurable amount can be delivered to a known volume of water to give a therapeutically effective concentration or a prophylactically effective concentration of the protein phosphatase inhibitor. The kit or the pharmaceutical composition therein may also comprise an additional medicament to augment further the protection of fish against microorganismic pathogens.

Specific embodiments of the invention disclose a kit comprising sodium orthovanadate and a catfish acceptable pharmaceutical carrier in solution form such that a volume in a premeasured container (e.g., eye dropper, vial, cup, etc.) is delivered to a known volume of water in a static flow, contained environment to give a therapeutically or prophylactically effective concentration of sodium orthovanadate.

Also, kits may be prepared to comprise additional medicaments, for example, antibiotics, fungicides, other protein phosphatase inhibitors, antiviral compounds including oligonucleotides and phosphothioate oligonucleotides, anti-inflammatory agents, etc. Optionally, a kit may also include instructions or guidance for the required dosage or amount of pharmaceutical composition to be delivered based on, for example, the volume of water in the contained environment, the number of fish suspended therein, the duration of treatment, etc.

It is contemplated that the present invention applies to teleost fish including domestic or pet fish, e.g., angels, goldfish, etc., and commercially-produced or farm grown fish, e.g., catfish, trout, salmon, eels, etc. These fish are grown in static-flow, contained aquatic environments, for example, in aquaria, ponds, tanks, pools, etc.

This invention contemplates the protection of fish against microorganismic pathogens. Protection is provided against enteric and opportunistic bacteria, including but not limited to *Edwardsiella ictaluric*, *Flexibacter columnaris*, *Aeromonas hydrophila* and *Edwardsiella tarda*, protozoan pathogens including opportunistic protozoans, e.g., *Ichthyophthirius multifiliis*, *tetrahymena*, etc., viruses and fungi. Thus, protection is provided against infectious diseases of teleost fish, e.g., enteric septicemia, columnaris disease, aeromonad septicemia, etc., diseases of fish associated with microorganismic pathogens.

More than one microorganismic pathogen or more than one disease can be treated at any one time. Thus, the present invention contemplates a use, a method, a pharmaceutical composition and a kit wherein an orthovanadate salt or a vanadate-mimetic protein phosphatase inhibitor is used in conjunction with an additional medicament to protect against microorganismic pathogens. For example, an antibiotic, a fungicide, an antiviral, an anti-inflammatory or a protein phosphatase inhibitor may be added together with orthovanadate or a vanadate-mimetic protein phosphatase inhibitor to protect fish from diseases associated with microorganismic pathogens.

In specific embodiments of this invention, protein phosphatase inhibitors were shown in vitro to enhance cytotoxicity of catfish nonspecific cytotoxic cells (NCC). Protein phosphatase inhibitors, for example, sodium fluoride and sodium vanadate, in millimolar concentrations, activated the cytotoxicity of NCC to lyse IM-9 target cells. The effects of the protein phosphatase inhibitors were additive. Combined treatment with two inhibitors, for example, sodium fluoride and sodium vanadate, indicated that the inhibitors recognized different classes of protein phosphatases, for example, fluoride specific for phosphoserine and vanadate for phosphotyrosyl groups, and their effects were additive.

In embodiments describing the increased cytotoxicity produced by protein phosphatase inhibitors, it was shown that the increases were significantly higher at low effector to target cell ratios (E:T). For example, greater increases in NCC cytotoxicity were observed at an effector to target cell ratio of 25:1 than 100:1.

In some embodiments of the invention, the in vitro enhancement of NCC cytotoxicity by protein phosphatase inhibitors was found in some cases to require the actual presence of the inhibitor molecule together with the NCC and target cells. For example, the activation of NCC cytotoxicity by treatment with sodium orthovanadate was largely retained when the orthovanadate-treated NCC were washed before being added to target cells. In contrast, the enhancement of NCC cytotoxicity by sodium fluoride was lost when the fluoride-treated NCC were washed prior to exposure to target cells. For optimum in vitro activation, protein phosphatase inhibitor molecules were maintained with the NCC during exposure to target cells.

NCC prepared from untreated fish exhibit different levels of constitutive cytotoxic activity, classified as low, medium and high. In stressed fish, NCC exhibit minimal or no in vitro cytotoxic activity. The ability of protein phosphatase inhibitors to stimulate NCC cytotoxic activity is greatest with NCC exhibiting minimal or no constitutive cytotoxicity. Competent, highly cytotoxic NCC cannot be superstimulated by these inhibitors. Suboptimal conditions, e.g., low effector to target cell ratios, or NCC from stressed fish can be activated to maximal or optimal levels of cytotoxicity by protein phosphatase inhibitor treatments.

In further embodiments of the invention, protein phosphatase inhibitors were shown to act also in vivo. When fish were exposed to a protein phosphatase inhibitor, for example, sodium orthovanadate, NCC prepared from such a vanadate-treated fish exhibited enhanced cytotoxicity. Thus, NCC cytotoxicity is activated in vivo as well as in vitro by vanadate or a vanadate-mimetic protein phosphatase inhibitor.

DETAILED DESCRIPTION OF THE INVENTION

Figure 1:
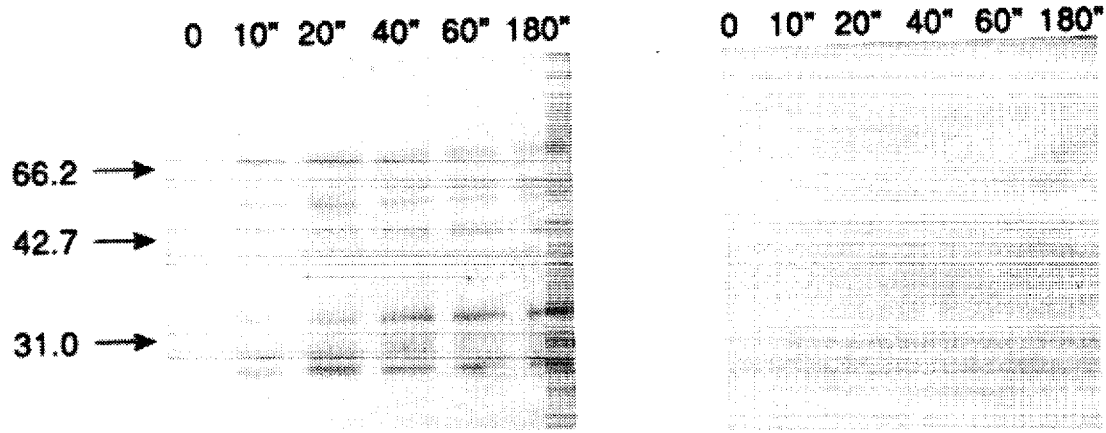
FIG. 1. Tyrosine phosphorylation of NCC membrane proteins following activation by mab 5C6. NCC were resuspended at $500\times10^6$/ml and 200 µl aliquots were incubated at 37° C. with either 125 µl ammonium sulfate precipitate mab 5C6 (left panel) or an isotype control (right panel). At the indicated timed intervals, the reactions were terminated by addition of 325 µl of 2×lysis buffer. Lysates were immunoprecipitated with mab 4G10, electrophoresed on 11% SDS-PAGE, blotted onto nitrocellulose, and probed with mab 4G10. Molecular weight markers are indicated by the arrows.

The following definitions are provided in order to provide clarity as to the intent or scope of their usage in the specification and claims.

Prophylactically effective amount or concentration as used herein refers to the amount or concentration of a compound administered to fish such that the compound is effective in preventing the fish from becoming infected in the presence of a microorganismic pathogen to which the fish is susceptible. For example, a prophylactic treatment is deemed to be effective in a situation where the mortality rate due to microorganismic pathogen challenge in fish pretreated with a vanadate-mimetic protein phosphatase inhibitor prior to challenge is reduced by between 25 and 100% of the rate observed in fish not pretreated with a vanadate-mimetic protein phosphatase inhibitor.

The prophylactically effective amount or concentration of the active compound takes into account the volume of the contained environment and also takes into consideration the number of fish housed therein.

Microorganismic pathogen as used herein refers to a microorganism that is pathogenic to fish and includes, but is not limited to, bacteria, protozoa, viruses, fungi and parasites.

Microorganismic infection as used herein refers to an infection in fish caused by a microorganismic pathogen which, if left untreated, may result in a disease characterized by abnormal behavior and/or physiology and may lead to death.

Therapeutically effective amount or concentration as used herein refers to the amount or concentration of a compound administered to fish infected with a microorganismic pathogen such that the infected fish is protected against the development or progression of an infection, disease, or mortality associated with the pathogen. For example, a therapeutic treatment is deemed to be effective in a situation where the mortality rate in fish challenged with a microorganismic pathogen and treated with a vanadate-mimetic protein phosphatase inhibitor is reduced by between 25 and 100% of the rate observed in infected, nontreated fish.

The therapeutically effective amount or concentration of the active compound takes into account the volume of the contained environment and also takes into consideration the number of fish housed therein.

Sodium orthovanadate or orthovanadate salt or orthovanadate or vanadate as used herein refers to a chemical composition that is sodium orthovanadate, $Na_3VO_4$, or that is a biological or chemical variant of sodium orthovanadate such that it exhibits biological activities, e.g., cytotoxicity, similar to sodium orthovanadate.

A vanadate-mimetic protein phosphatase inhibitor as used herein refers to an inhibitor of a protein phosphatase that mimics or simulates a biological or pharmacological action or effect of sodium orthovanadate in vivo in fish on protection against microorganismic pathogens or in vitro in fish on activation of NCC cytotoxicity. For example, sodium fluoride is considered to be a vanadate-mimetic protein phosphatase inhibitor, since sodium fluoride inhibits a protein phosphatase and mimics the biological action of sodium orthovanadate in activating isolated NCC.

Contained aquatic environment or contained environment as used herein refers to an aquarium, tank, pool, or pond having static flow, and not flow through, water.

Domestic fish as used herein refers to fish that are not produced or raised on farms on a large scale for commercial purposes. The term domestic fish includes, but is not limited to, fish obtained from pet stores and fish kept as pets, for example, angels, goldfish, etc.

Stressed fish as used herein refers to fish that are exposed to a condition of stress, for example, a toxicant, a drastic temperature change, handling, etc. Stressed fish are defined as having NCC with little or no cytotoxicity and as having increased susceptibility to infection when compared to normal fish.

Cytotoxicity as used herein refers to the ability of a cell to destroy, kill or lyse a target cell. Cytotoxicity can be measured experimentally by the release of $^{51}Cr$ from a target cell upon exposure to a cytotoxic cell, as described in Example 1 or by other assays known in the art.

Target cells as used herein refer to cells that undergo destruction or lysis due to the cytotoxicity associated with a cytotoxic cell. The target cells used in in vitro cytotoxicity studies described herein were IM-9 human Epstein Barr Virus (EBV) transformed β lymphocytes.

NCC as used herein refers to nonspecific cytotoxic cells from teleost fish.

Effector to target cell ratio (E:T) as used herein refers to the number of effector cells exposed to a given number of target cells. For example, E:T refers to the ratio given by the number of effector cells divided by the number of IM-9 target cells in, for example, a cytotoxicity assay.

A pharmaceutical carrier as used herein refers to a carrier and/or stabilizer and/or binder which is employed in conjunction with the active component (e.g., vanadate or a vanadate-mimetic protein phosphatase inhibitor), and may be any one of a wide variety of carriers. Representative examples of standard carriers are, for example, buffers, mineral oil, alum, synthetic polymers, etc. Water per se is not considered to be a carrier. Carriers for pharmaceutical compositions are well known in the art and the selection of a suitable carrier is deemed to be within the scope of those skilled in the art. The selection of a suitable carrier is also dependent on several factors, for example, on the solubility of the active component and upon the manner in which the pharmaceutical composition is to be administered, for example, as a solution or in a solid form, e.g., tablet, capsule, cubes, flakes, etc.

A prophylactic treatment as used herein refers to the administration to a fish of a prophylactically effective amount or concentration of an active component (e.g., a vanadate-mimetic protein phosphatase inhibitor) such that the active component is effective in preventing the fish from becoming infected in the presence of a microorganismic pathogen to which the fish is susceptible.

A therapeutic treatment as used herein refers to the administration to a fish infected with a microorganismic pathogen of a therapeutically effective amount or concentration of an active component (e.g., a vanadate-mimetic protein phosphatase inhibitor) such that the active component is effective in protecting the infected fish against the development or progression of an infection, disease or mortality associated with the pathogen.

The instant disclosure advocates that an equilibrium between protein kinase and protein phosphatase activities is operational in NCC activation. The importance of membrane phosphorylation and protein kinase activities to the regulation of signaling responses in NCC was evaluated.

Several protein kinase inhibitors, e.g., the isoquinoline-sulfonamide derivatives H-7, H-8, and HA1004 and genistein, were tested for their effects on NCC killing of IM-9 target cells. H-7 is an inhibitor of protein kinase C (PKC), to a lesser extent it inhibits cyclic nucleotide kinases and has no effect on calmodulin mediated responses; H-8 has a limited effect on PKC and is more inhibitory of cyclic nucleotide dependent kinases; HA1004 has no effect on PKC and inhibits mostly cyclic nucleotide dependent kinases.

H-7 and H-8 produced a time and dose dependent inhibition of NCC cytotoxicity (Table 1). The level of inhibition of NCC activity was approximately 35% compared to approximately 60–90% produced by the same concentration of H-7 against human NK cells. Higher concentrations of H-8 were required to inhibit NCC activity (Table 2); approximately 150 μM concentration of H-8 gave inhibition levels comparable to that obtained with approximately 30 μM H-7. In contrast to H-8, H-7 is known to have almost no effect on protein kinase C activity [Asano, T. et al. (1984) *J. Pharmacol. Exp. Ther.* 231:141].

When HA1004 was tested (Table 3), NCC activity was increased, indicating that cAMP-cGMP dependent kinases participate in signaling and in regulating cytotoxicity in NCC. This observation for HA1004 is opposite to that observed with human T-cells and NK cells.

Genistein, a protein tyrosine kinase (PTK) inhibitor, almost completely inhibited NCC activity in a dose-dependent fashion (Table 4). Genistein has been shown to inhibit PTK activity and to have no effect on serine/threonine phosphorylation in NK cells [Stahls et al. (1992) supra; June et al. (1990) *Proc. Natl. Acad. Sci.* 87:7722; Mustelin et al. (1990) *Science* 247:1158]. NCC, similar to NK cells from higher vertebrates, appear to utilize tyrosine phosphorylation as a prerequisite step in cytotoxicity.

The inhibitory or activating effect of the above compounds was compared to the effects of the calcium ionophore A23187 and the mab 5C6 antibody to an NCC receptor protein (Table 5). Treatment with A23187 resulted in a strong activation of NCC cytotoxicity, whereas treatment with mab 5C6 produced a moderate level of activation. Pretreatment with either H-7, HA1004, genistein or mab 5C6 prior to the addition of A23187 ionophore did not appear to be additive and did not influence the final level of activation of NCC cytotoxicity which was that obtained with the A23187 ionophore alone. It did appear that A23187 was able to overcome the inhibition produced by treatment of NCC with H-7 or genistein. When mab 5C6 was used instead of the A23187 ionophore to activate cytotoxicity (Table 6), mab 5C6 did not completely overcome the inhibitory effects of H-7 or of genistein in co-treatments.

Activation of NCC by mab 5C6 binding increased tyrosine and serine phosphorylation of membrane proteins. Several NCC membrane phosphoproteins were identified using a commercially available monoclonal antibody, mab 4G10. The anti-phosphotyrosine mab 4G10, which is specific for phosphotyrosine-containing proteins of all species, does not react with phosphoserine or phosphothreonine. Western blot analysis of membranes obtained from NCC following stimulation with mab 5C6 indicated that about five groups of proteins falling within the molecular weight ranges of approximately 20–28, 32–34, 44–47, 55–58, and 70–72 kD (FIG. 1) were phosphorylated upon binding of mab 5C6 to NCC. Only NCC proteins were phosphorylated during activation. Percoll-purified NCC (FIG. 2) were treated with mab 5C6. The proteins phosphorylated by purified cells were not different from those observed from the mixed-cell population described in FIG. 1.

Figure 3:
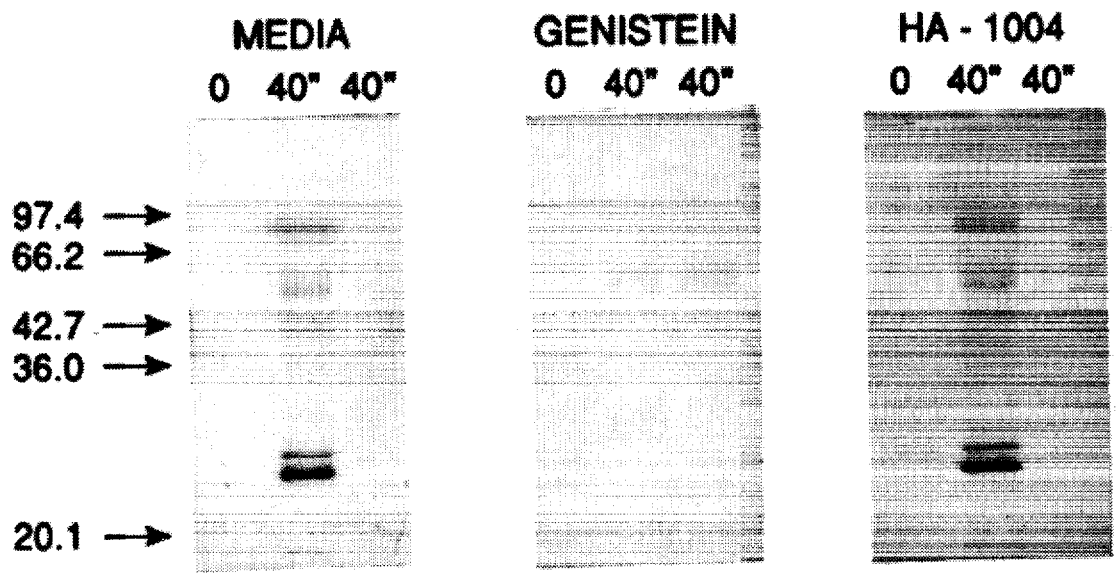
FIG. 3. Effects of genistein on tyrosine phosphorylation in fish NCC. Fish NCC were incubated with media, genistein (100 µg/ml), or HA1004 (30 µM) for two hours prior to activation for zero time with mab 5C6 (left lane) and 40 sec with either mab 5C6 (middle lane) or an irrelevant IgM isotype control (right lane). Reactions were stopped by addition of lysis buffer and lysates were processed as explained in the legends to FIGS. 1 and 2.

To define the specificity of the tyrosine phosphorylation following activation by mab 5C6, NCC were pretreated for two hours with media, genistein, or HA1004 (FIG. 3). The cells were then washed and incubated with mab 5C6 for 0 (left lane) or 40 sec (middle lane) and with an irrelevant IgM isotype control mab for 40 sec (right lane). Specific protein phosphorylation was not observed in cells treated with the protein tyrosine kinase inhibitor, genistein, but did occur in the presence of HA1004.

Compared to similar experiments done with NK [Einspahr et al. (1990) *J. Immunol.* 145:1490] and T-cells [Ferris et al. (1989) *J. Immunol.* 143:870], phosphotyrosyl groups in NCC membranes were more closely associated with the molecular weight ranges of T-cell proteins than NK phosphoproteins. The kinetics of expression of tyrosyl phosphorylated substrates following mab 5C6 stimulation of NCC indicated that by 20 sec post-mab 5C6 binding, the full complement of substrates were phosphorylated. These data are equivalent to T-cell responses following stimulation with mab anti-CD3 [Peyron et al. (1989) *Cellular Signaling* 1:313]. Furthermore, immunoprecipitation experiments using anti-phosphoserine polyclonal antibody showed increased phosphorylation following mab 5C6 binding to NCC compared to control levels.

Only a few proteins on NK cells from any species (e.g., CD16/FcR in humans, NKR-P1 in rats, NK1.1 in mice) are associated with increased phosphorylation of membrane protein tyrosine following binding of a monoclonal antibody. There appears to be only one protein on fish NCC and on human and rat NK cells [Evans et al. (1993) Scan. J. Immunol. 37:131] that may have nonhistocompatibility antigen binding capacity. Monoclonal antibody (e.g. mab 5C6) binding to this protein triggers NCC cytotoxicity.

NCC activation by mab 5C6 binding leads to increased expression of some members of the proto-oncogene family of kinases. Immunoprecipitation experiments demonstrated that mab 5C6 binding to NCC was associated with increased levels of expression of cytosolic $p56^{lck}$, $p60^{src}$, and $p59^{fyn}$. Additionally, molecular weight isoforms of these kinases were produced following mab binding. This activity has previously only been associated with TcR and Fc receptor (NK cells) binding. Some of the commercial mabs against mammalian oncogene products are cross-reactive with catfish kinases. This is not surprising because the oncogene kinases belong to a large family of kinases, all of which share significant amino acid homology.

NCC activation appeared to correlate with increased kinase production and increased protein phosphorylation. Membrane protein phosphorylation could be maintained through an equilibrium between cellular kinase and phosphatase activities. The observation that NCC activation required the presence of phosphorylated tyrosine residues suggested that prolonged maintenance of protein phosphorylation by the presence of protein phosphatase inhibitors might have an additional activation effect on NCC function.

Figure 4:
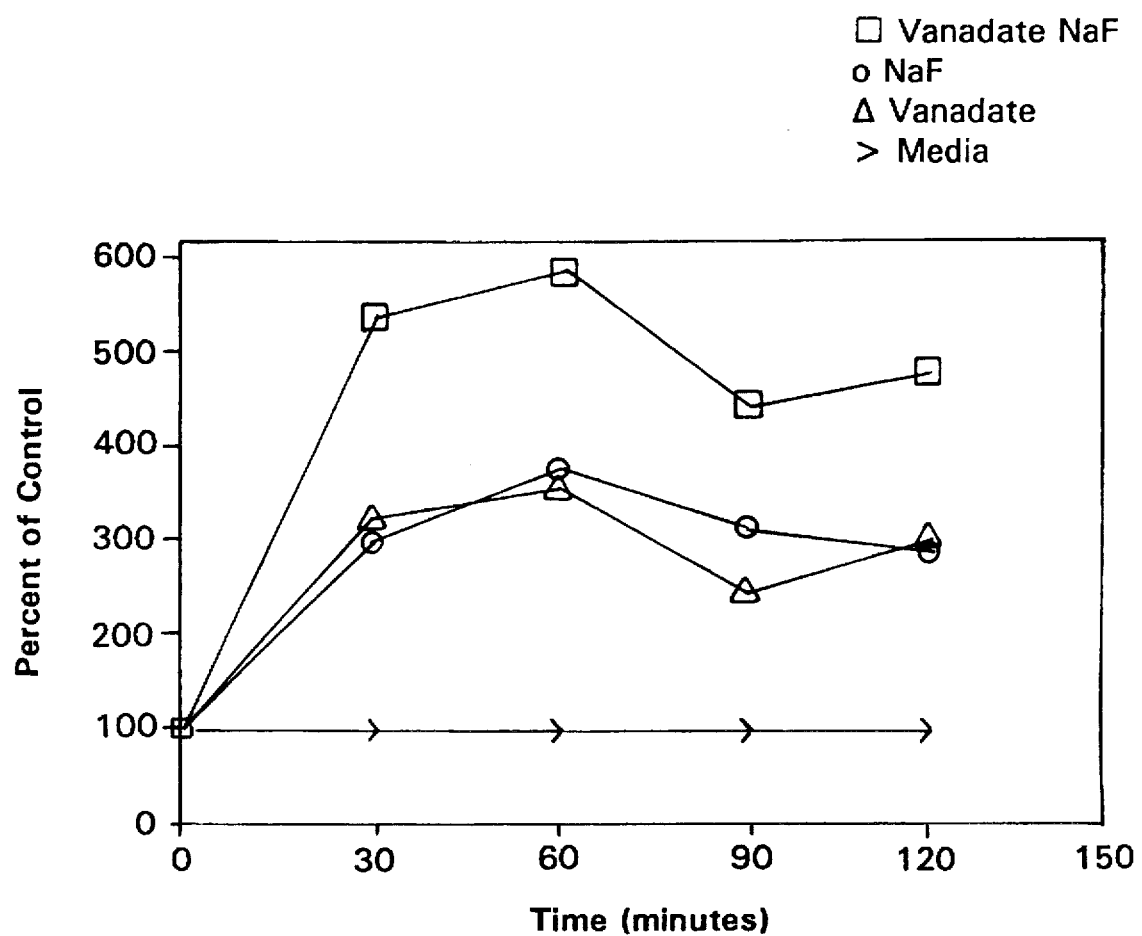
FIG. 4. Individual and combined effects of phosphatase inhibitors on NCC cytotoxicity, NCC ($7\times10^5$ cells) were incubated with either media ($\Diamond$), vanadate ($\Delta$) (5 mM). NaF (o) (20 mM), or both vanadate and NaF ($\square$) for the indicated time periods before addition to labeled IM-9 target cells.

The effect of three major protein phosphatase inhibitors on the cytotoxicity of NCC is disclosed in Table 7. The major types of PPhase inhibitors investigated were lithium chloride (a specific inhibitor of phosphotidylinositol phosphate phosphatase), sodium fluoride, phosphoserine/phosphothreonine specific inhibitor) and sodium orthovanadate (to a large part specific for phosphotyrosine). As shown in Table 7, lithium chloride had little effect on cytotoxicity when compared to fluoride or vanadate. Sodium vanadate and sodium fluoride enhanced the destruction of IM-9 target cells by approximately six- to eightfold. A time-course of the individual and combined effects of vanadate and fluoride showed that maximum activation of cytotoxicity occurred after a 60 minutes incubation time with NCC and that vanadate and fluoride actions in increasing target cell destruction were additive (FIG. 4).

An important characteristic of the increased cytotoxicity produced by the protein phosphatase inhibitors (Table 7) was that the increases were significantly higher at the lower effector:target cell ratios, i.e., at 25:1 rather than 100:1. This suggested that the inhibitors were stimulating increases in individual cell activation responses rather than causing increased numbers of NCC to be produced.

Figure 5:
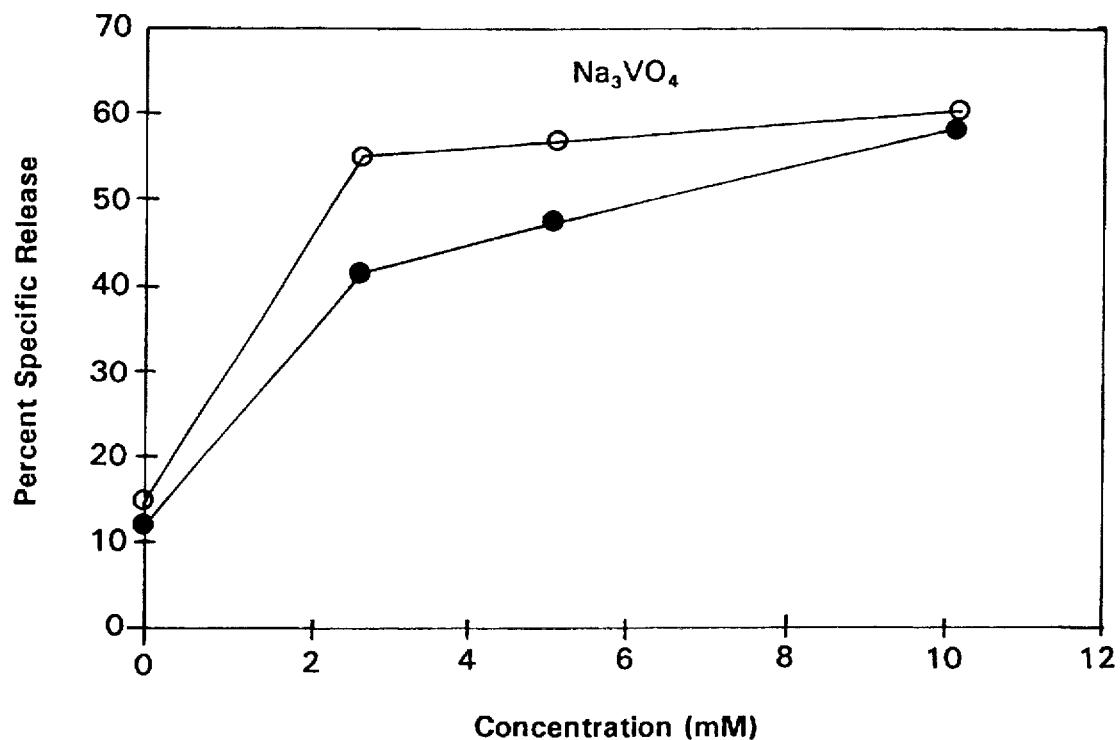
FIG. 5. Effects of removal of $Na_3VO_4$ on NCC activation. NCC were harvested, incubated for three hours, washed, counted and added to duplicate tubes containing either media alone or media containing 2.5, 5 and 10 mM vanadate. Following a 90 minutes incubation time, the cells were either washed and resuspended in media (closed circles) or added directly (open circles) to wells containing $^{51}$chromium labeled IM-9 target cells (E:T ratio 40:1).

In some cases, the enhancement of NCC cytotoxicity by protein phosphatase inhibitors was found to require the actual presence of the inhibitor molecule in conjunction with NCC and the target cells. The activation of NCC cytotoxicity by treatment with sodium vanadate was shown (FIG. 5) to be largely retained when the vanadate-treated NCC were washed before being added to the target cells. In contrast, the enhancement of NCC cytotoxicity by sodium fluoride (FIG. 6) was lost when the fluoride-treated NCC were washed prior to exposure to target cells. In control experiment, the inhibitors themselves were either not toxic to labeled IM-9 target cells (lithium chloride and sodium fluoride) or produced less than 10% nonspecific toxicity (sodium vanadate). Thus, removal of vanadate produced slightly reduced levels of NCC cytotoxicity, whereas removal of fluoride almost completely obliterated NCC activation.

The kinetics of the activation responses suggested that the action is direct, probably at the membrane level of the NCC, because activation occurred rapidly and because optimum (in vitro) activation required that the inhibitors be present with the target cells for optimum responses. The protein phosphatases which regulated cytotoxicity were most probably membrane NCC proteins and also the protein substrates of the inhibited protein phosphatase were most likely found principally in the membrane of NCC.

"Stressed" fish are those having NCC which exhibit no or very little cytotoxic activity. NCC prepared from "stressed" fish, e.g., catfish, which exhibited essentially zero levels of cytotoxicity (Table 9), produced significantly increased lysis of target cells when the stressed fish were treated with either sodium vanadate or sodium fluoride. A much higher concentration of fluoride than vanadate was required to achieve significant levels of activation.

The ability of vanadate (FIG. 7) and sodium fluoride (FIG. 8) to stimulate NCC activity was compared in three different types of fish, e.g., catfish: those with low, medium and high cytotoxicity. The greatest effects were observed with the low cytotoxicity groups. It would appear that competent, highly cytotoxic NCC cannot be "super" stimulated by these inhibitors. Suboptimal conditions (low E:T ratios) or "stressed" NCC can be activated to normal levels of activity by protein phosphatase inhibitor treatments. Phosphatases appear to regulate an early phase of NCC cytotoxicity. The most logical conclusion from these data is that the inhibitors act directly on membrane protein phosphatases which participate in regulating NCC cytotoxicity and that inhibition of protein phosphatase activity results in the production of a highly activated NCC.

Combined treatment with both inhibitors (FIG. 4) indicated that the inhibitors apparently recognized different classes of phosphatases (e.g., fluoride specific for phosphoserine and vanadate for phosphotyrosyl groups) and that their effects were additive. Treatment with relatively high concentrations of fluoride or vanadate was not toxic to NCC and did not apparently have any lethal or other deleterious effects on the cell populations.

Figure 9:
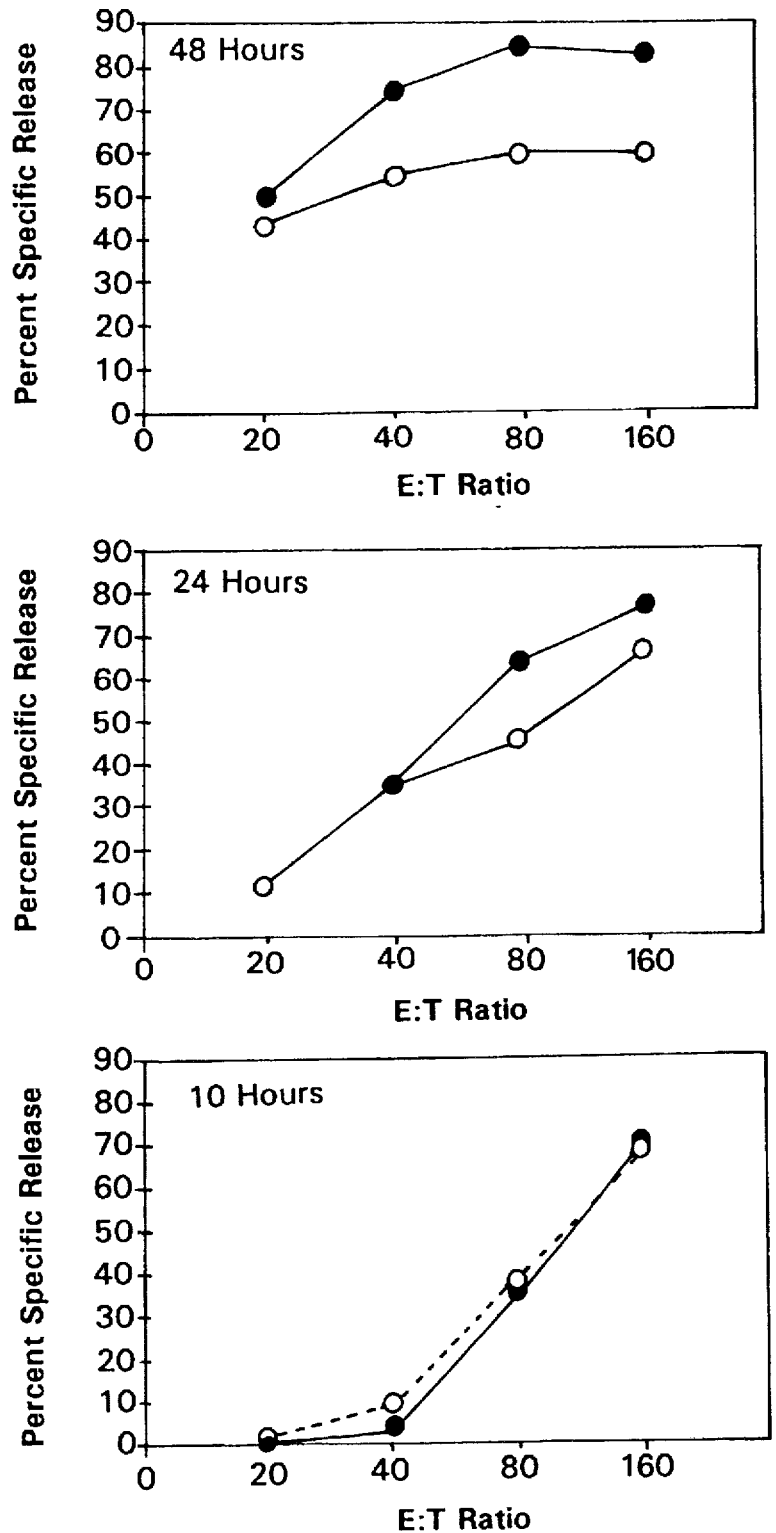
FIG. 9. In vivo NCC responses to vanadate treatment. Catfish were acclimated in 10 gal tanks for 24 hours prior to treatment. Vanadate was added directly to the tanks and cytotoxicity assays of NCC from treated and control fish were conducted at 10, 24 and 48 hours post-treatment.

NCC cytotoxicity was shown to be augmented also in vivo by phosphatase inhibitors. Concentrations of vanadate used in in vitro experiments (i.e., 2.5 mM and greater) were found to be lethal to live fish, whereas vanadate concentrations of 0.05 mM or less were well tolerated. Catfish exposed to 0.05 mM sodium orthovanadate for approximately 24 hours had NCC with enhanced cytotoxic activities (FIG. 9). The largest differences between nontreated and treated NCC were found at 48 hours post-initiation of treatment. The in vivo effect of vanadate was not due to fluctuations in the total number of cells nor in the percentage of NCC in anterior kidney tissue (Table 10).

In vivo treatment with vanadate induced protection against infections in fish. Catfish, exposed 30–45 minutes to a dosage of bacteria, e.g., *Edwardsiella ictaluri*, that produces an acute fulminating disease with 90–100% mortality, were protected by treatment with micromolar concentrations of vanadate. Catfish treated with between approximately 10 µM to approximately 25 µM vanadate for 18–24 hours (FIG. 10) survived the acute phase of the disease with significantly less mortality than controls. Significantly more control, nonvanadate-treated fish died, presumably of septicemia, compared to vanadate-treated fish. Tissue obtained from several different infected fish were positive for Edwardsiella. This intervention model successfully showed that vanadate can be used to significantly lower mortality and morbidity from *E. ictaluri* infections.

Figure 11:
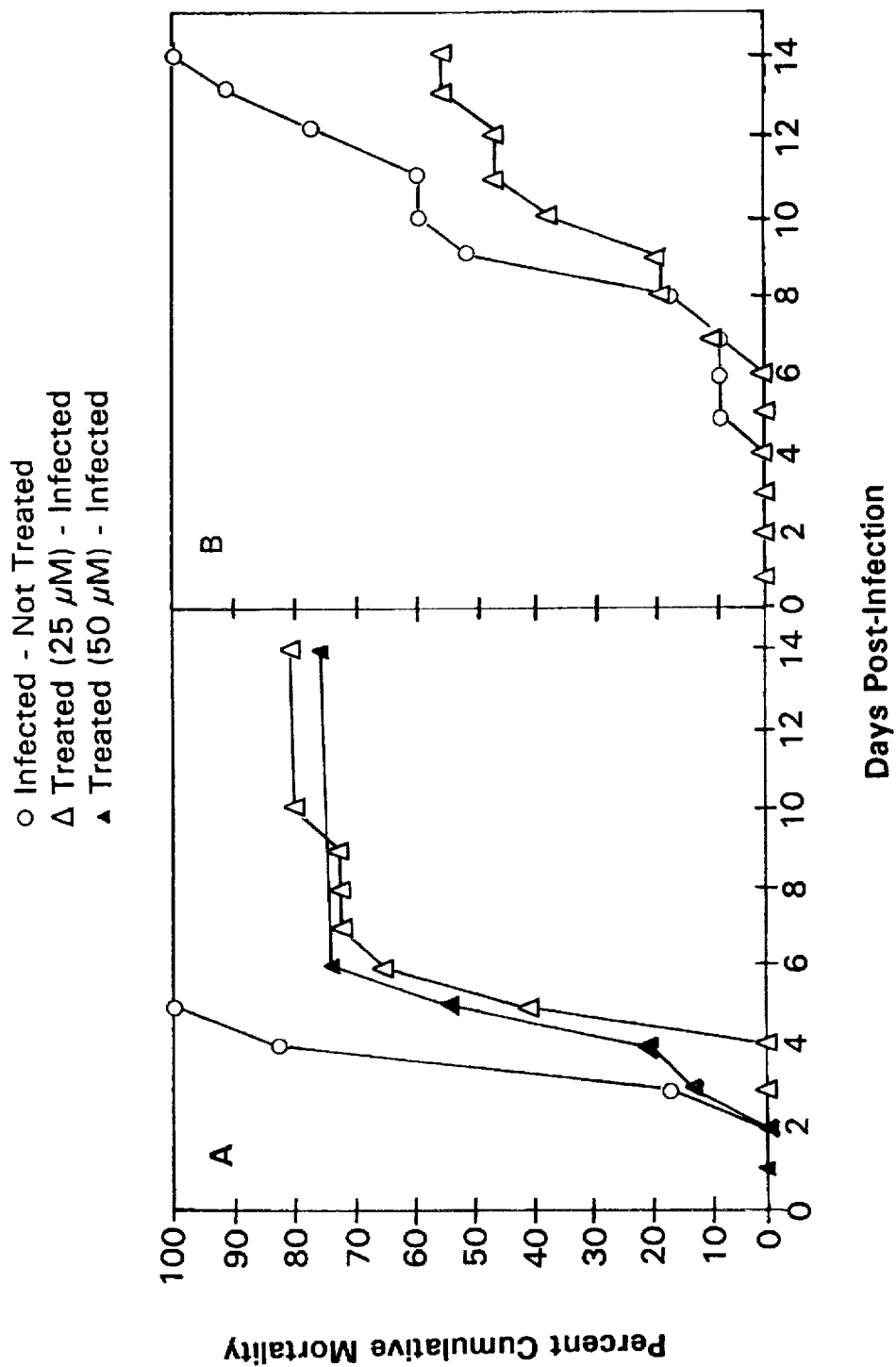
FIG. 11. Effects of treatment of catfish with vanadate prior to infection with *E. ictaluri*. In two different experiments (A and B), catfish were treated with vanadate (indicated concentrations) 48 hours prior to infection with Edwardsiella. Percent cumulative mortality for each treatment group is given. Numbers of fish were 12–15/group/experiment. At 28 days post-infection (experiment B), all treated catfish were still alive.

In vivo pretreatment with vanadate afforded prophylactic protection against microorganismic infection in fish. Since noninfected catfish treated with 0.05 mM orthovanadate produced significantly increased cytotoxicity 48 hours post-treatment, this level of vanadate was used for prophylactic pretreatment of catfish 48 hours prior to infection with Edwardsiella. Pretreatment of catfish with 0.05 mM did produce a decrease in mortality (FIG. 11) even under conditions where the fish were exposed to a high dosage of bacteria, for example, dosages such that 100% mortality occurred in untreated control fish 10–15 days post-infection. These data clearly demonstrated that vanadate produced a significant population of resistant catfish in the presence of the highly pathogenic Edwardsiella. Prophylactically effective concentrations of sodium orthovanadate for protection of catfish from Edwardsiella comprise between approximately 5 μM and 50 μM.

It will be immediately recognized and appreciated by those in the art that the concentration of vanadate or a vanadate-mimetic protein phosphatase inhibitor that is effective therapeutically or prophylactically is dependent on various factors and may have to be adjusted and take into consideration such factors as, for example, the type of fish (for example, freshwater fish such as trout, salmon, catfish, eels, etc.), the size or stage of growth of the fish, the number of fish in a contained aquatic environment, the temperature of the water, etc.

Sodium vanadate or a vanadate-mimetic protein phosphatase inhibitor can be incorporated, together with a carrier or stabilizer acceptable to fish, into a pharmaceutical composition for use in the protection of teleost fish against infection caused by microorganismic pathogens. The pharmaceutical composition may further comprise additional medicaments, which include but are not limited to, an antibiotic such as tetracycline, ampicillin, penicillin, erythromycin, etc., a fungicide such as sulfamethazine, sulfathiozole, sulfadiazine, sulfamerazine, etc., an antiviral compound such as an oligonucleotide, a phosphothioate, etc., an anti-inflammatory agent such as naprosyn, motrin, voltaren, etc., and a protein phosphatase inhibitor.

In other embodiments of the invention, a pharmaceutical composition comprising sodium orthovanadate or a vanadate-mimetic protein phosphatase inhibitor is marketed commercially as a kit for the protection of fish against infection caused by microorganismic pathogens. In the kit, the pharmaceutical composition is present in liquid or solid form, for example, as a solution, tablet, grains, flakes, powder, cube, capsule or other forms known in the art, such that it can be easily dispensed, for example, with an eye dropper, a vial, a cup, a spoon, etc. A measurable or a premeasured amount of the pharmaceutical composition in the kit can be delivered to a given amount of aqueous medium (e.g., water, buffer, etc.) in a contained environment (e.g., aquarium, tank, pool, pond, etc.), to give a final concentration of vanadate or vanadate-mimetic protein phosphatase inhibitor that is a therapeutic or a prophylactic concentration in the treatment of fish against microorganismic pathogens.

Guidelines or directions for use of the pharmaceutical composition may be included in the kit. The dosage of the pharmaceutical composition may be specified, based on, for example, the volume of water, the number of fish, the type of fish, the size of fish, the state of the fish (normal, stressed, infected, etc.) in the contained aquatic environment and, also, the type of microorganismic pathogen involved. Directives for the frequency and duration of the treatment as well as instructions for changing the water during a treatment schedule may also be enclosed in the kit.

The use of sodium orthovanadate or other vanadate-mimetic protein phosphatase inhibitors in therapeutic or prophylactic treatments of commercially grown fish elicits the important question concerning safety of resultant fish or fish products for human consumption. Prior art suggests that vanadate is not toxic and does not produce irreversible tissue changes characteristic of cell transformation. For example, oral administration of vanadate (15 μM in drinking water) to rats did not appear to be toxic, nor to show any deleterious or pathogenic effects. Also, the effects observed after treatment of rats with vanadate (e.g., normalization of blood glucose levels in diabetic animals) were reversible within two days after suspension of vanadate treatment [Meyerovitch et al. (1987) *J. Biol. Chem.* 262:6658]. There was no evidence that vanadate produced any irreversible changes.

Sodium orthovanadate or vanadate-mimetic protein phosphatase inhibitors can also be used to protect fish against protozoan parasites, for example, *Ichthyophthirius multifiliis* (Ich). This protozoan has a worldwide distribution and affects all freshwater fish. A membrane determinant on Ich is recognized by NCC [Graves et al. (1985) *J. Immunol.* 134:78] and NCC are capable of lysing this parasite [Graves et al. (1985) *Comp. Immun. Microbiol. Infect. Dis.* 8:43].

In a disease model using Ich, the parasite is maintained in vivo in catfish. The life cycle of Ich consists of two parts, a parasitic feeding stage and a reproductive stage. The parasitic stage lasts from three days to several months, depending on the water temperature (optimum is 21°–23° C.). Optimally, detachment occurs by three to five days. Within about six hours of leaving the host, the parasite must begin encystment and reproduction in order to produce progeny, which are infective for 20 to 96 hours.

Intervention and prophylactic models suitable for Ich appear to be similar to bacterial infection models. For example, Ich is propagated by placing an infected catfish in an aquarium with normal fish. Under optimum conditions of temperature, water quality, etc., fish begin to die within about 15 days post-infection. Sodium orthovanadate or a vanadate-mimetic protein phosphatase inhibitor is added to the tanks either prior to or after infection to prevent or to treat fish against infection or disease caused by Ich.

The protozoan parasite-NCC interaction is a model where the effector cell comes in direct contact with Ich to elicit cytotoxicity. Because vanadate and vanadate mimetic protein phosphatase inhibitors significantly increase in vivo and in vitro NCC activity (especially from stressed fish), these protein phosphatase inhibitors are most likely to stimulate anti-protozoan resistance. Similar models can be used for other types of protozoa that are pathogenic to fish, particularly to freshwater fish.

This invention provides a method for the production of a nonspecific immunity. Without wishing to be bound by any theory explaining the mechanism of action, Applicants postulate that vanadate treatment may initiate a rapid NCC infiltrate into the intestine. This tissue is the focal point of the immune activity during Edwardsiella infections. The basic mechanism of altered resistance produced at this site could thus be: (1) vanadate initiates NCC migration into the catfish intestinal mucosa and submucosa (and/or resident NCC may respond); (2) activated NCC then elaborate and secrete cytokines (e.g., interferons); (3) these cytokines in turn induce macrophage and heterophil activation (infiltration, phagocytosis, cytokine production and release, etc.). A vanadate-mimetic protein phosphatase would behave in similar fashion in producing nonspecific immunity.

Vanadate and a vanadate mimetic protein phosphatase could thus exacerbate a very active, efficient and effective nonspecific immune response. The effector cell required to potentiate this activity would be NCC.

NCC interact with and kill bacteria. The mechanisms of bacterial inactivation and death involve many pathways; cytokine production and release play a role in these responses. For teleost NCC, it is possible that NCC do not directly lyse bacteria and, instead, elaborate and secrete interferons and other cytokines which activate phagocytic cells.

The present invention relates to the relevance of protein phosphatase inhibitors to the protection of other species and other types of natural killer cells. For example, the CRC cells (tissue cultured cells obtained from peripheral blood of leukemic F344 rats) are perhaps more interesting (e.g., another model to study the effects of vanadate on altering immunosuppressed NK function) because these are in vitro maintained rat leukemic NK cells which have spontaneously lost cytotoxicity against YAC-1 target cells. Sodium fluoride produces a 3-fold increase in the lytic activity of these cells. It is possible that the discovery of this activity of protein phosphatase inhibitors may have widespread importance for studies of mechanisms of signaling in all vertebrates. Additionally, these inhibitors may have clinical importance in circumstances of immunosuppression, immunodeficiency and other conditions of altered immune activity.

Almost all classes of protein phosphatase inhibitors including zinc chloride, EDTA, sodium orthovanadate (vanadate), lithium chloride, sodium fluoride (fluoride), and okadaic acid exhibit preferred binding specificities for different types of protein phosphatase based on substrate specificity of the protein phosphatases; binding with certain regulatory domains on the protein phosphatases; dependence on the presence of divalent cations; or in fact a combination of any one of a number of different factors. Zinc preferentially binds to phosphotyrosyl phosphatases with the highest specificity of any inhibitor [Salcedo et al. (1993) *J. Exp. Med.* 177:1475]. Although fluoride and vanadate have apparent preferences for phosphoserine and phosphotyrosine [Atkinson et al. (1992) *J. Immunology*, 148:2194], respectively, these inhibitors by no means have a high degree of fine specificity for one kind of phosphorylated amino acid. Vanadate and fluoride inhibit a wide variety of phosphatases [Chan et al. (1986) *J. Biol. Chem.* 261:9890; Imes et al. (1987) *Analy. Biochem.* 161:316; Lin et al. (1986) *Biochem. J.* 235:351; Tamura et al. (1986) *Biochem. Biophys. Res. Comm.* 140:212–218; Boivin et al. (1986) *Biochem. Biophys. Res. Comm.* 134:557; Chernoff et al. (1985) *Arch. Biochem. Biophys.* 240:135]. Clearly, many of these protein phosphatases have different specificities for tyrosine, serine, and threonine. In some studies where both types of inhibitors have been compared for activity, vanadate but not fluoride inhibited protein phosphatase activity [Tung et al. (1987) *Analy. Biochem.* 161:412; Okada et al. (1986) *Biochem. J.* 239:155]. Similarly, fluoride, but not vanadate inhibited human prostate gland phosphotyrosyl protein phosphatase [Li et al. (1984) *J. Biochem.* 138:45] and calcineurin-mediated dephosphorylation [Pallen et al. (1985) *Biochem.* 24:4727].

The notion that phosphatases might be involved in the process of regulation of NCC cytotoxicity is compatible with several other observations. For example, phosphatase inhibitors (e.g., LiCl) was required in experiments to detect increased levels of phosphotidylinositol metabolites (i.e., $PIP_3$) which appear during cell triggering responses. Lithium chloride specifically inhibited phosphotidylinositol phosphate phosphatase activity. Other phosphatase inhibitors (zinc chloride, sodium fluoride, okadaic acid, etc.) have been used in numerous studies to demonstrate the build-up of phosphoproteins following agonist binding. Also, mab 5C6 binding to an NCC receptor molecule activated cytotoxicity Evans et al. (1990) supra, initiated the release of free cytoplasmic calcium [Evans et al. (1990) *Dev. Comp. Immunol.* 14:295; Evans et al. (1992) supra] and caused increased levels of IP3 production. Increasing and prolonging levels of protein phosphorylation could thus be associated with increased cytotoxicity.

The present studies which show that alterations in dephosphorylation by phosphatase inhibitors affect cytotoxicity are supported by studies demonstrating that vanadate stimulated cellular carbohydrate biosynthetic pathways. Vanadate has insulin-mimetic activity as demonstrated by studies showing: augmentation of insulin binding [Fantus et al. (1990) *Endocrin.* 127:2716], prolongation of insulin activity [Fantus et al. (1990) supra], stimulation of glucose oxidation [Schechter et al. (1980) supra], and stimulation of glycogen synthetase activity [Tamura et al. (1984) Supra]. Vanadate directly activated kinases in rats [Gill et al. (1988) supra], in transformed human B-cells [Earp et al. (1983) supra] and rat adipocytes [Ledbetter et al. (1988) supra]. Oral administration of vanadate to rats (15 µM in the drinking water) caused normalization of blood glucose levels in diabetic animals. In rats, vanadate also stimulated glucose transport into muscles and liver and improved cardiac performance. These effects were reversible within two days following termination of feeding [Meyerovitch et al. (1987) supra]. In these studies, there was no evidence that vanadate produced any irreversible changes in these treated rats.

Additional models to suggest that phosphatases might participate in signaling responses in NCC are studies of the glycoprotein CD45 (although this molecule does not exist on NCC). CD45 participates in T-cell activation processes [Ledbetter et al. (1988) Supra; Kiener et al. (1989) supra; Shaw et al. (1991) supra; Livanainen et al. (1990) supra; Odum et al. (1991) supra]. Specifically, the substrate recognized by CD45 appears to be $p56^{lck}$ [Mustelin et al. (1989) supra]. This kinase is probably activated by dephosphorylation of $Tyr^{505}$ which precedes autophosphorylation, activation of the zeta chain [Salcedo et al. (1993) supra], etc.

After entry into cells, most of the vanadate is reduced to the vanadyl (IV) ion. Both forms can produce firm complexes with protein. The biochemical actions of these two forms differ significantly. For example, the vanadyl ion has little effect on inhibiting $Na^+/K^+$ ATPase activity, whereas this ATPase is significantly inhibited by vanadate [Cantley et al. (1979) *J. Biol. Chem.* 254:1781; North et al. (1984) *J. Biol. Chem.* 259:4971]. Vanadate has pleiotropic (direct) effects on different amino acid-specific phosphatases; vanadate may even act on some kinases; and vanadate may act in the nonreduced and/or reduced form at the outer membrane or in the cytosol, respectively.

It will be appreciated by those of ordinary skill in the art that the objects of this invention can be achieved without the expense of undue experimentation using well known variants, modifications, or equivalents of the methods and techniques described herein. The skilled artisan will also appreciate that alternative means, other than those specifically described, are available in the art to achieve the functional features of the vanadate or vanadate-mimetic protein phosphatase inhibitors described herein and how to employ those alternatives to achieve functional equivalents of the present invention capable of protecting fish against microorganismic pathogens. It is intended that the present invention include those variants, modifications, alternatives and equivalents which are appreciated by the skilled artisan and encompassed by the spirit and scope of the present disclosure.

The following Examples are provided for illustrative purposes only and are not intended to limit the scope of the invention.

EXAMPLE 1

MATERIALS AND METHODS (1) Fish

Outbred channel catfish (*Ictalurus punctatus*) of both sexes weighing 20–60 g were obtained from local commercial farms. Fish were maintained in 50-liter aquaria containing uv-filtered and temperature-controlled (20°–25° C.) water. The diet consisted of pelleted fish food (Purina Catfish Startena, Ralston Purina Co., St. Louis, Mo.). Fish were net captured, lightly anesthetized, and killed, and tissue was removed.

(2) Media and Antibodies

All cell culture was done using RPMI 1640 (Cellgro. Media Tech. Washington, D.C.) containing 10% fetal bovine serum (Sigma Chemical Co., St. Louis, Mo.) as previously described [Evans et al. (1988) supra]. Media used in assays containing fish cells was adjusted to an osmolarity of 250 mOsm/kg $H_2O$.

The monoclonal antibodies were 5C6 [specificity previously reported in Evans et al. (1988) supra] and isotype control mab TGE (specificity against porcine transmissible gastroenteritis virus). Anti-phosphotyrosine mab 4G10 (specific for phosphotyrosine-containing proteins of all species and does not react with phosphoserine or phosphothreonine) was purchased from Upstate Biotechnology, Inc., Lake Placid, N.Y.

(3) Reagents

Protein kinase inhibitors H-7 [1-(5-isoquinolinesulfonyl)-2-methylpiperazine di-HCl] (Calbiochem, LaJolla, Calif.: No. 371955, lot 187591); H-8 [N-(2-(methylamino)ethyl)-5-isoquinolinesulfonamide di-HCl] (Calbiochem: No. 371958, lot 91X002); and HA1004 [N-(2-guanidoethyl)-5-isoquinolinesulfonamide di-HCl] (Calbiochem: No. 371964, lot 90X026) were used. Stock solutions of each inhibitor were 600 µM in sterile PBS (pH 7.4) and stored at 4° C. in the dark until used.

The protein tyrosine kinase (PTK) inhibitor, genistein, (Calbiochem: No. 34834, lot 145091) was made fresh prior to each treatment. A stock solution was prepared at 100 µg/ml DMSO. Calcium ionophore A23187 (Sigma Chemical Co.) was prepared at $10^{-2}M$ concentration in DMSO and stored at −80° C. Aliquots were thawed prior to treatment and diluted to the indicated concentrations in RPMI 1640 (10% FBS).

(4) Effector and Target Cells

All cells were cultured in RPMI 1640 containing 10% FBS and were maintained as previously described [Evans et al. (1988) supra]. To prepare NCC, fish were lightly anesthetized with ethyl m-aminobenzoate (Sigma Chemical Co.) in water and sacrificed. Anterior kidney cells were removed and single cell suspensions were prepared [Graves et al. (1984) supra].

IM-9 target cells were used in cytotoxicity assays. These are human Epstein Barr Virus (EBV) transformed lymphocytes maintained in RPMI 1640. Cells were grown in stationary suspension cultures and were maintained at approximately $1\times10^6$ cells/ml.

To determine if more than one type of cell participated in producing phosphorylation of tyrosyl groups, NCC were purified by Percoll density-gradient centrifugation as previously described [Evans et al. (1987) supra] and compared by Western blot analysis with unfractionated cells.

(5) Costimulation Assay

NCC were preincubated for two to three hours in RPMI 1640 (10% FBS) (37° C.), harvested, and added to the indicated treatments in different molar concentrations as indicated. Incubation was two hours and cells were either washed or not washed before addition to $^{51}$Cr-labeled IM-9 target cells (4- to 6-hour cytotoxicity assays).

(6) Cytotoxicity Assay

A $^{51}$Cr release assay was used to determine cytotoxicity. Target cells at $1-2\times10^6$ cells/ml were labeled with 100 µCi of sodium chromate (Amersham, Arlington Heights, Ill.). NCC effector cells were treated as previously described [Evans et al. (1988) supra], centrifuged (500 g), and resuspended in media and added at different E:T ratios to the labeled target cells in round-bottomed 96-well microtiter plates. This mixture was incubated (25° C.) for 4–6 hours and 100 µl of each supernatant was removed to determine radioactivity (Beckman Biogamma II Counter; Beckman Instruments, Irvine, Calif.). The results are expressed as either percentage specific release (SR)=[(test release—spontaneous release)/(total release—spontaneous release)]×100; percent inhibition=[(percentage control SR—percentage test SR)/percentage control SR]×100; and percentage increase= (percentage test SR—percentage control SR)/percentage control SR.

(7) Modulation of Cytotoxicity

NCC were obtained as previously described [Graves et al. (1984) supra]; Evans et al. (1984) supra]. Cells were preincubated for 3 hr in RPMI 1640 (10% FBS). NCC were then washed and resuspended at $20\times10^6$ cells/ml, and 35 µl aliquots were added to test tubes containing 315 µl media only (media control) or media containing the indicated treatments. After 2 hr incubation, the cells were mixed with $^{51}$Cr-labeled IM-9 target cells and incubated for 4–6 hours (37° C.). Supernatants were harvested and cytotoxicity levels were calculated as previously described.

(8) Determination of Protein Tyrosine Phosphorylation

NCC were harvested, washed (2×) in PBS (pH 7.4), and resuspended ($500\times10^6$ cells/ml PBS). Activation of NCC was done by adding mab 5C6 or isotope mab control at timed intervals to $1\times10^8$ cells. Incubation was terminated by addition of an equal volume of ice-cold 2×lysis buffer (1%, v/v, Triton X-100; 500 mM NaCl; 100 mM Tris-HCl; pH 7.5; 2 mM EDTA; 10 mM LiCl; 20 mM NaF; 2 mM $Na_3VO_4$; 2 mM PMSF; and 20 µg/ml leupeptin). The last three reagents of the lysis buffer were prepared fresh prior to use. At time zero, antibody was added at the same time as lysis buffer.

Cell lysates were then incubated for 20 minutes on ice and centrifuged for 15 minutes (Beckman Microfuge). Supernatants were added to 50 µl or protein G-conjugated agarose beads (Sigma Chemicals Co.) containing mab 4G10. This mixture was next incubated 18 hours (shaking, 4° C.). Beads were washed (3×) with 1× lysis buffer, and the final pellet was eluted with 50 µl 1× SDS buffer. Tubes were vortexed and centrifuged and supernatants were removed and boiled for 5 minutes. Samples were loaded onto 11% SDS-PAGE and transferred to nitrocellulose membranes for Western blot analysis [Jaso-Friedmann et al. (1992) supra].

(9) In vivo Treatment with Sodium Orthovanadate

Fish were treated by immersion in 10 gal (static flow) tanks containing the appropriate inhibitor concentrations in 15 liters of dechlorinated water (19°–20° C.). All fish were acclimated to tank conditions 24 hours prior to treatment. Each tank housed twenty fish (approximately 4–5 inches in length). At 24 hour intervals 50% of the water was changed.

EXAMPLE 2

DETERMINATION OF PROTEIN KINASE ACTIVITIES ON NCC CYTOTOXICITY (1) Isoquinolinesulfonamide Derivatives The isoquinolinesulfonamide derivatives H-7 [1-(5-isoquinolinesulfonyl)-2-methylpiperazine di-HCl], H-8 [N-(2-methylamino)ethyl)-5-isoquinolinesulfonamide di-HCl] and HA1004 [N-(2-guanidoethyl)-5-isoquinolinesulfonamide di-HCl] were analyzed on NCC lysis of IM-9 target cells. IM-9 target cells are human EBV transformed lymphocytes maintained in culture. H-7 is known to bind directly to the catalytic site on protein kinase C (PKC) or to cyclic nucleotide-dependent protein kinases [Kawamoto, S. et al. (1984) *Biochem. Biophy. Res. Commun.* 125:258; Hidaka, H. et al. (1984) *Biochem.* 23:5036; Atluru, D. et al. (1990) *Cell. Immunol.* 129:310; Jung, L.K.L. et al. (1988) *Cell. Immunol.* 117:352; Nel, A. E. et al. (1987) *J. Immunol.* 139:2230]. H-8 is known to have less of an effect on PKC but to be more inhibitory of cyclic nucleotide-dependent kinases than H-7. HA1004 is frequently used as a control for PKC inhibitors because it inhibits other classes of protein kinases other than PKC [Asano, T. et al. (1984), supra; Procopio, A. D. G. et al. (1989) *Cell. Immunol.* 114:470].

To determine time and dose-dependent responses, NCC were treated with H-7 for one to three hours and then either target cells were added, or H-7 was removed prior to addition of the IM-9 target cells. A three hour treatment (Table 1) with an inhibitor concentration of 60 μM produced significant inhibition of cytotoxicity. An inhibitor concentration of 30 μM required approximately a two hour treatment to produce a similar inhibition response. The inhibitory effects of H-7 were at the effector cell level because washing prior to the addition of the target cells did not substantially affect the cytotoxicity when compared to leaving the inhibitor in the assay.

Significantly higher concentrations of the cyclic nucleotide-dependent kinase inhibitor H-8 were required to inhibit NCC activity (Table 2). H-8 was used because it was previously shown to have almost no effect on PKC activity [Asano, T. et al. (1984) supra]. A concentration of approximately 150 μM of H-8 was required to produce levels of inhibition comparable to that obtained with an approximately 30 μM concentration of H-7. Similar experiments were conducted with the cAMP- and cGMP-dependent PK inhibitor HA1004. At 30 and 60 μM concentrations, a significant increase in cytotoxicity was observed (Table 3). The increase was at the effector cell level because removal of HA1004 prior to addition of the IM-9 target cells did not reduce the augmentation of cytotoxicity.

(2) Genistein

To indirectly determine the requirements for tyrosine residue phosphorylation during NCC activation, the tyrosine-specific protein kinase inhibitor genistein [Akiyama T. et al. (1987) *J. Biol. Chem.* 262:5592] was added to NCC. As shown in Table 4, almost 100% inhibition of cytotoxicity was observed following treatment with 142 μg/ml concentration of genistein, while a genistein concentration of between approximately 14 and approximately 57 μg/ml produced greater than 50% inhibition.

(3) Costimulation with A23187

To further investigate this inhibitory effect, a costimulus experiment was done using a calcium ionophore, e.g., A23187, combined with the various inhibitors and activators of NCC activity. Pretreatment of NCC with A23187 produced an almost identical increase in cytotoxicity regardless of the identity of the first treatment. The levels of cytotoxicity were not additive in the presence of secondary activating stimuli (e.g., mab 5C6 or HA1004) and inhibitors H-7 and genistein did not produce any reductions in A23187 activation (Table 5).

(4) Costimulation with mab 5C6

In a second costimulus experiment mab 5C6 was used (instead of A23187) to activate cytotoxicity (Table 6). The significant difference in this stimulus-induced experiment was that mab 5C6 did not completely overcome the inhibitory effects of H-7 or of genistein co-treatment.

EXAMPLE 3

DETERMINATION OF THE LEVEL OF TYROSINE PHOSPHORYLATION FOLLOWING MAB 5C6 ACTIVATION

Figure 2:
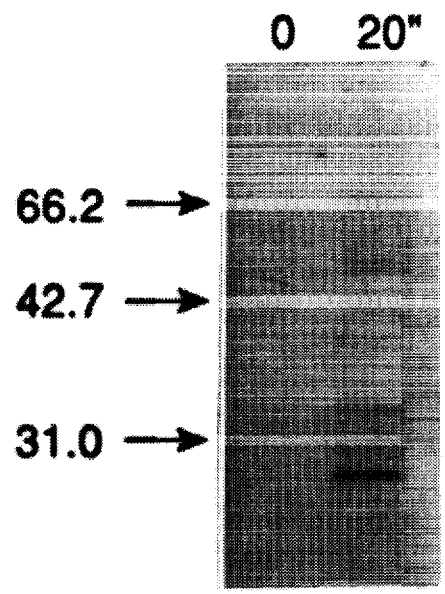
FIG. 2. Tyrosine phosphorylation of Percoll-enriched NCC. Fish NCC were centrifuged for 15 minutes at 500 g on a 45.5% Percoll cushion. The cells at the interphase were harvested, washed, and treated with mab 5C6 for 0 and 20 sec before addition of 2×lysis buffer. Lysates were electrophoresed, blotted on nitrocellulose, and probed with mab 4G10.

Anti-phosphotyrosine mab 4G10 (specific for phosphotyrosine-containing proteins of all species and does not react with phosphoserine or phosphothreonine) was used in Western blot experiments to determine the level of tyrosine phosphorylation following mab 5C6 activation. NCC were activated by treatment with mab 5C6 and cells were solubilized, immunoprecipitated with protein G-bound mab 4G10, and subjected to SDS-PAGE and Western blot analysis. A time-course experiment is shown in FIG. 1. A rapid increase in the phosphorylation of tyrosine residues occurred between 10 and 180 sec following mab 5C6 binding (left panel). The zero time points show the results when both mab 5C6 and lysis buffer were added to the cells at the same time. At least five different molecular weight proteins were phosphorylated, ranging in weight from 20 to 70 kD (left panel). The right panel shows the same experiment using an isotope control mab as the activating mab.

Next, control experiments were done to determine that only NCC proteins were phosphorylated during activation (anterior kidney cells in FIG. 1 were not purified). Percoll-purified NCC (FIG. 2) were treated with mab 5C6 for 0 and 20 sec followed by solubilization and analysis as described for FIG. 1. The proteins phosphorylated by purified cells were not different from those observed from the mixed-cell population.

To further determine the specificity of the tyrosine phosphorylation following activation by mab 5C6, NCC were pretreated for two hours with media, genistein, or HA1004 (FIG. 3). The cells were then washed and incubated with mab 5C6 for 0 (left lane) or 40 sec (middle lane) and with an irrelevant IgM isotope control mab for 40 sec (right lane). Specific protein phosphorylation was not observed in cells treated with the protein tyrosine kinase inhibitor, genistein, versus HA1004.

EXAMPLE 4

EFFECT OF PROTEIN PHOSPHATASE INHIBITORS ON NCC CYTOTOXICITY (1) In vitro

Membrane phosphorylation is maintained through a delicate equilibrium between cellular kinase and phosphatase activities. The observation that NCC activation requires the presence of phosphorylated tyrosine residues suggested that prolonged maintenance of protein phosphorylation by the presence of phosphatase inhibitors might have an additional activation effect on NCC function. Table 7 shows that incubation of effectors with different concentrations of a protein phosphatase inhibitor, e.g., sodium vanadate or sodium fluoride, enhanced the killing of IM-9 target cells by as much as six- to eightfold over control levels at the lower effector:target (E:T) ratios. Lithium chloride had moderate or no effect on cytotoxicity. A time-course of the individual and combined effects of vanadate and NaF showed that maximum activation of cytotoxicity occurred after a 60-minute incubation time with NCC, and that their action of increasing target cell killing is additive (FIG. 4).

Figure 6:
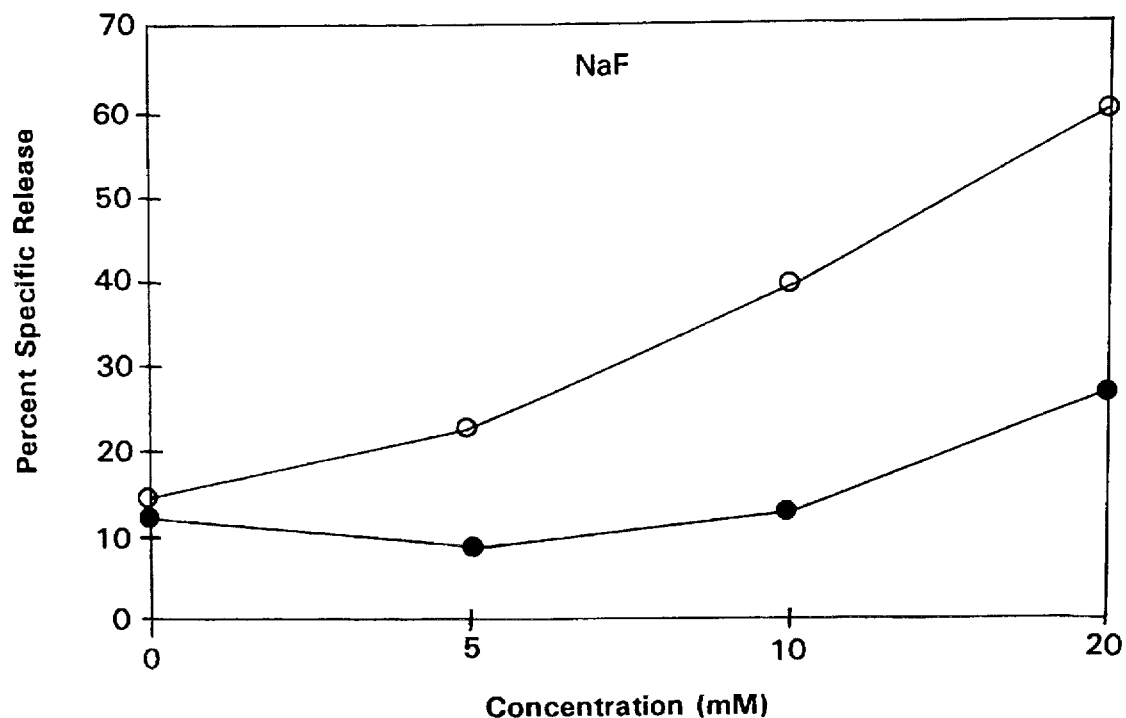
FIG. 6. Effects of removal of NaF on NCC activation. NCC were harvested, incubated for three hours in media, washed, counted and added to duplicate tubes containing media alone or in the presence of 5, 10 and 20 mM NaF. Following a 90 minutes treatment time, NCC were either washed (closed circles) or added directly (open circles) to wells containing labeled IM-9 target cells (E:t ratio 40:1).

In further studies, NCC were treated with different concentrations of protein phosphatase inhibitors for two hours and labeled IM-9 target cells were added for a four-hour microcytotoxicity assay (Table 8). For "healthy" fish, only small increases in cytotoxicity were produced at the highest effector:target cell (E:T) ratio. The greatest effects of the protein phosphatase inhibitors were seen at the lowest (25:1) E:T ratio. To determine if the activating effects of the protein phosphatase inhibitors were reversible, NCC were treated for 90 minutes with NaF and vanadate and then the inhibitors were removed prior to addition of the labeled target cells. Toxicity control experiments revealed that 20 mM LiCl or NaF was not toxic to labeled IM-9 targets and 10 mM vanadate produced less than 10% nonspecific toxicity (e.g., release of chromium$^{51}$ from IM-9 targets). Normal NCC produced significant increased cytotoxicity following treatment with vanadate (FIG. 5) or NaF (FIG. 6) in the presence of the inhibitors. Removal of vanadate produced slightly reduced levels of cytotoxicity, whereas NaF removal almost completely obliterated activation (FIG. 6).

The protein phosphatase inhibitors were evaluated to determine whether they had effects on NCC from fish which had virtually no cytotoxicity (i.e., stressed fish). A common observation in fish exposed to stress, e.g., toxicants, drastic temperature changes, handling, etc., is the temporary loss of NCC activity. "Normal" activity does not return to this type of stressed fish for several days to weeks. In Table 9, control, stressed fish had essentially no cytotoxicity. Both fluoride (group 1) and vanadate (group II), individually, augmented cytotoxic activity from essentially zero to relatively high levels. The combined treatment effects (groups III-V) were additive. Lithium chloride (5 and 10 mM) either individually or in combination had no effects on cytotoxicity.

Figure 7:
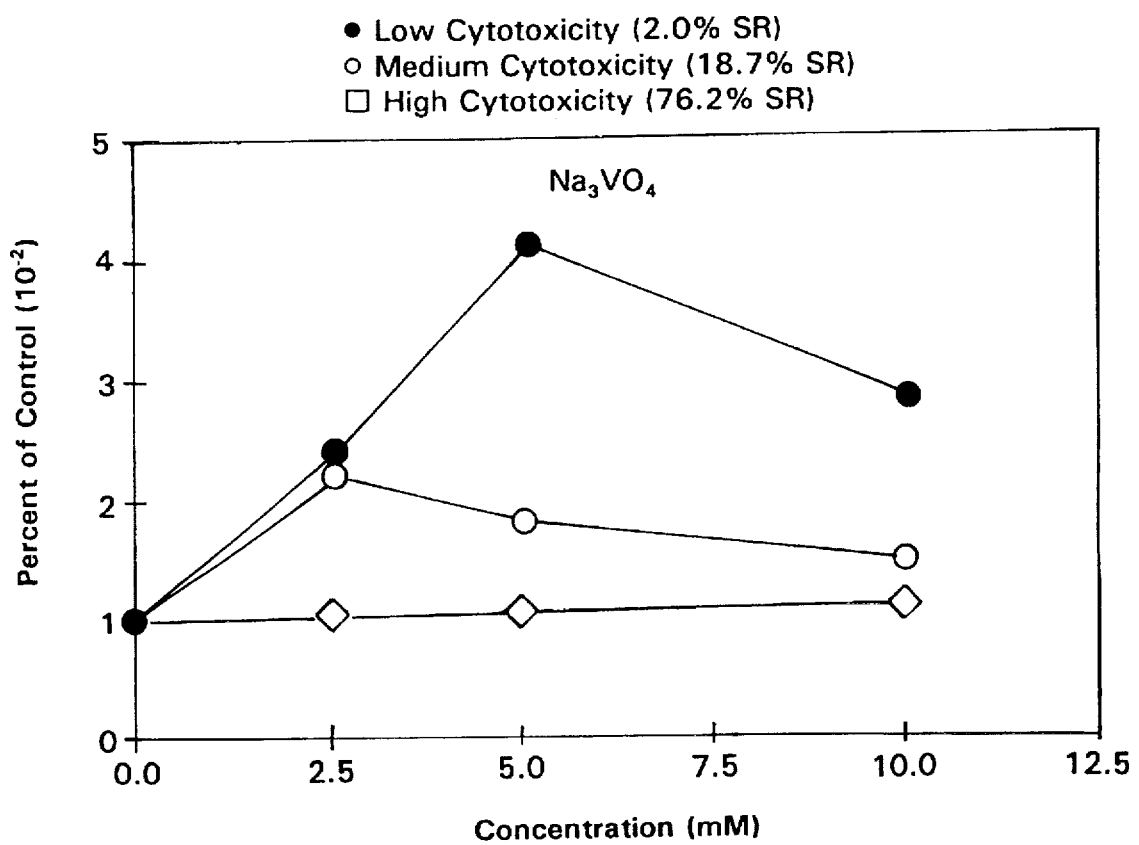
FIG. 7. Effects of $Na_3VO_4$ on NCC with different levels of cytotoxicity. NCC were harvested from anterior kidneys of fish from three different sources. The cells were incubated in media for three hours, washed, counted and added to test tubes containing either media alone or media with 2.5, 5 and 10 mM vanadate. Following a two hours incubation time, the effectors were added to wells containing labeled IM-9 cells at a 40:1 E:T ratio.
Figure 8:
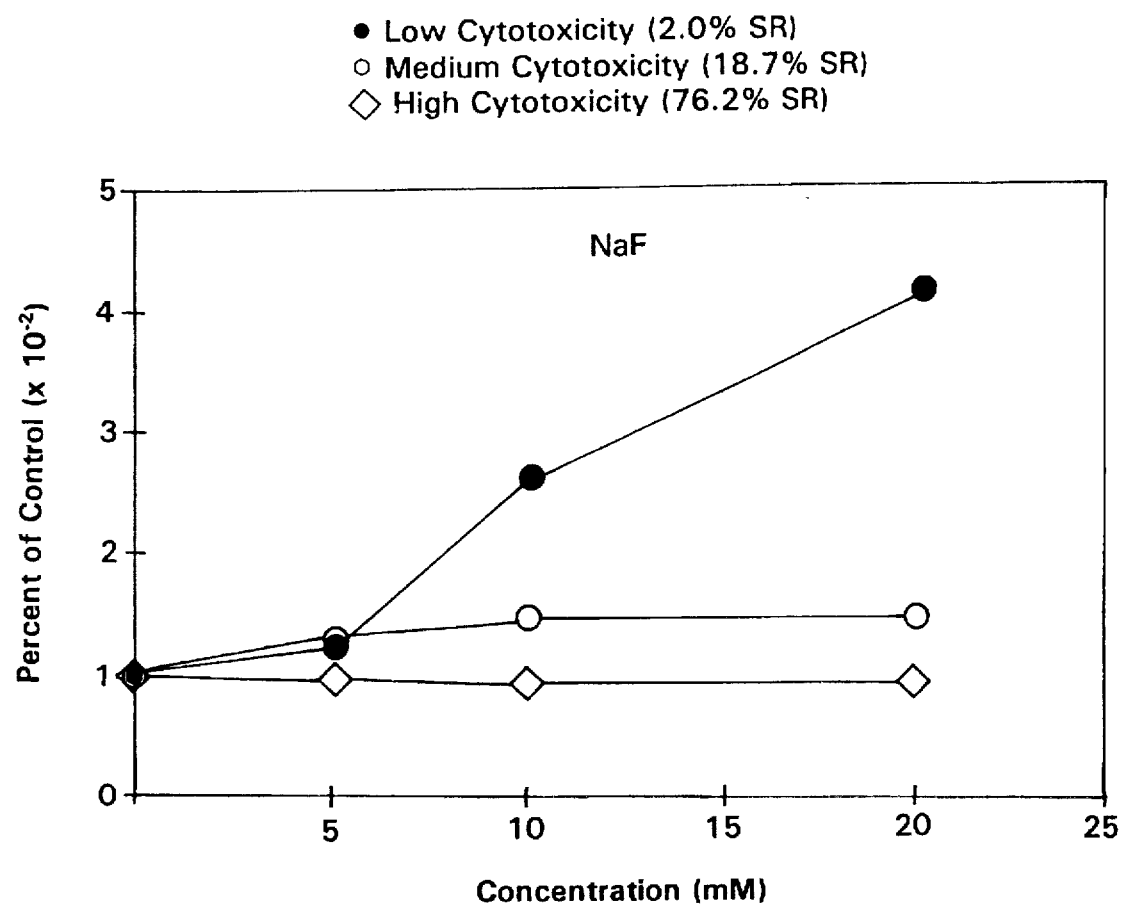
FIG. 8. Effects of NaF on NCC with different levels of cytotoxicity. NCC were harvested from anterior kidneys of fish from three different sources. The cells were incubated in media for three hours, washed, counted and added to media or media with 5, 10 and 20 mM NaF. Following a two-hour incubation, NCC were added to wells containing $^{51}$chromium labeled IM-9 target cells for a final E:T ratio of 40:1.

The relationship between inherent levels of cytotoxicity and NCC responsiveness to inhibitor treatment was further examined by comparing the effects of the protein phosphatase inhibitors on fish with low, medium and high cytotoxicity levels. In FIG. 7, NCC from catfish with 2.0% control Specific Release were highly responsive to vanadate treatment. A similar relationship was observed following treatment with fluoride (FIG. 8). Much higher concentrations of fluoride than vanadate were required to achieve activation responses. High responders were almost refractory to inhibitory treatment.

(2) In Vivo

To determine if phosphatase inhibitors produced similar in vivo actions compared to in vitro treatments, fish were treated by immersion in vanadate. First, vanadate concentration titrations were done to determine a toxicity profile. In vivo delivered (by immersion) concentrations greater than 0.125 mM were toxic to catfish. When catfish were exposed one time to 0,025–0,100 mM vanadate, toxic responses were not observed. Vanadate was readily soluble in tank water; mixing of the vanadate into the tank water was fast and complete within minutes.

To determine the ability of vanadate to act in vivo to activate NCC responses, fish were treated by immersion with 0.050 mM vanadate and cytotoxicity was determined at 10, 24 and 48 hours post-treatment. FIG. 9 shows that 50 μM vanadate produced large increases in cytotoxicity by 48 hours. It appeared that in vivo inhibition of phosphatase activity significantly increased NCC lysis of target cells. Fluoride was not used in these experiments because of the high concentrations required to produce in vitro effects; and also because, in general, toxicity reactions were produced by the phosphatase inhibitors by much lower concentrations in vivo than in vitro.

To determine if the increased cytotoxicity was associated with changes in percent composition of small lymphocytes (i.e., NCC) and in total numbers of cells, total cell counts and percent NCC in anterior kidney tissue were determined. Table 10 shows that although some changes occurred in both parameters, notable large fluctuations were not seen.

EXAMPLE 5

THERAPEUTIC EFFECT OF VANADATE AGAINST MICROORGANISMIC INFECTION

Figure 10:
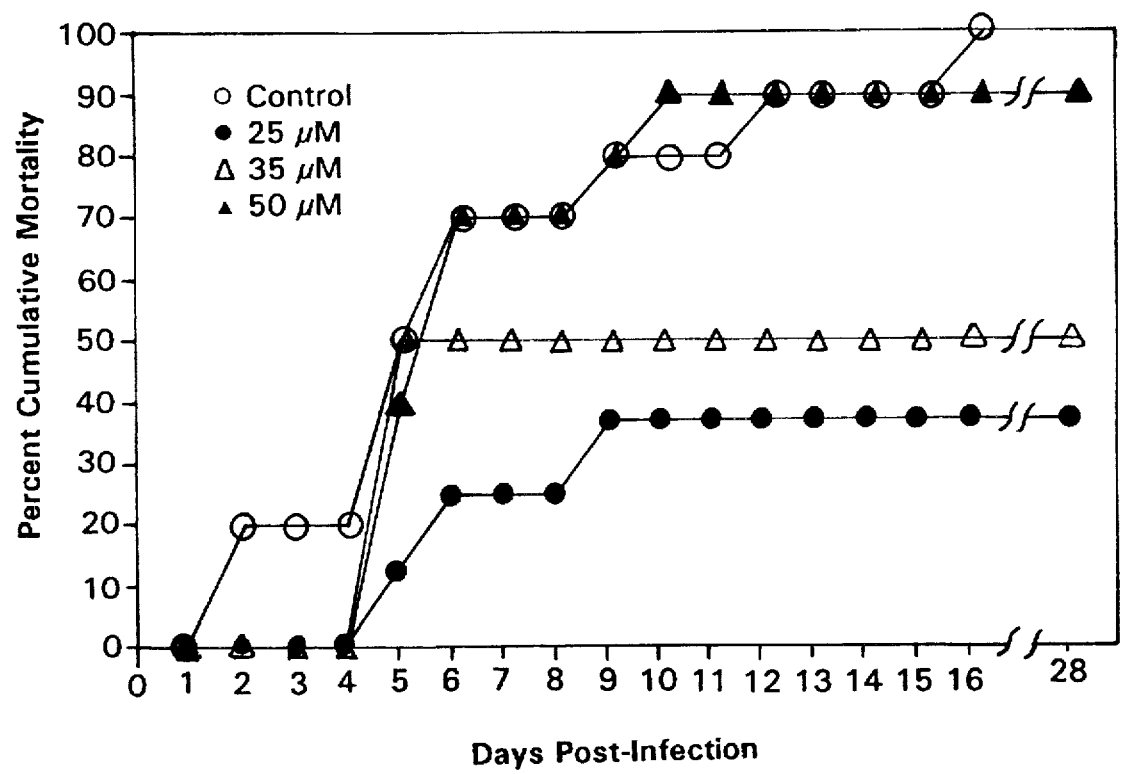
FIG. 10. Cumulative mortality of catfish infection with *Edwardsiella ictaluri*. Fish were first infected (by immersion) with $10^7$–$10^8$ bacteria/ml (approximately 1 McFarland Turbidity unit). Fish were next placed in tanks containing the indicated concentrations of vanadate. Fish were treated for 18 hours and subsequently water was changed daily and fish were fed ad libitum.

Catfish fingerlings, approximately 3–4 inches in length, were first infected by immersion for approximately 30–45 minutes with approximately $10^6$–$10^7$ bacteria (*Edwardsiella ictaluri*) per ml. This dosage produces an acute fulminating disease with 100% mortality by approximately 10–15 days post-infection. Approximately two hours following infection, different concentrations of vanadate were added to the tanks. As shown in FIG. 10, fish treated with 0.0125–0.025 mM vanadate survived all phases of the disease with significantly less mortality than controls. Tissue obtained from different infected fish were positive for Edwardsiella. This intervention model successfully demonstrated that vanadate, when delivered post-infection, can be used to significantly lower mortality in fish.

EXAMPLE 6

PROPHYLACTIC EFFECT OF VANADATE AGAINST BACTERIAL INFECTION

Noninfected catfish treated with 0.05 mM sodium orthovanadate produced significantly increased cytotoxicity 48 hours post-treatment. Thus, catfish were treated (by immersion) with 0.05 mM vanadate for 48 hours prior to infection with *Edwardsiella ictaluri*.

First, as shown in FIG. 11A, pretreatment with vanadate prior to bacterial infection produced a 27% reduction in mortality. The infected (but not vanadate treated) group had a 92% death rate by day 6 post-infection and 100% mortality by day 9. The infectious dosage of bacteria was too high in this experiment to allow assessment of efficacious concentrations of vanadate.

In a second experiment, as shown in FIG. 11B, fewer bacteria were used, such that 90–100% mortality occurred in the control, infected, nonvanadate treated group by day 13–14. At this time interval, i.e., 13–14 days post infection, the vanadate (0.05 mM)-pretreated group had a reduced mortality of 54%. Again, in order to more accurately assess the most efficacious, prophylactic dosage of vanadate, the bacterial load must be reduced. These data clearly demonstrate that vanadate produced a significant population of resistant catfish in the presence of the highly pathogenic Edwardsiella.

EXAMPLE 7

PROTECTIVE EFFECTS OF VANADATE AGAINST PROTOZOAN PARASITE PROTECTION

The protozoan, *Ichthyophthirius multifiliis* (Ich), has a worldwide distribution and affects all freshwater fish. NCC recognize a membrane determinant on Ich [Graves et al. (1985) supra and NCC are capable of lysing this parasite [Graves et al. (1985) supra.

The pathogenesis of Ich is different from *Edwardsiella ictaluri* infection. The common properties are that both are relatively acute diseases (thus rely on nonspecific/natural immune mechanisms in naive hosts) and both can cause large economic losses. NCC become activated in Ich infections. NCC lyse Ich and vanadate activates NCC.

The following protocol is used to test the effects of sodium orthovanadate or a vanadate-mimetic protein phosphatase inhibitor against infection or disease caused by Ich. The parasite is maintained in vivo in catfish. The life cycle of Ich consists of two parts, a parasitic feeding stage and a reproductive stage. The infective form (theront) attaches and enters the epithelium of a catfish within 5–15 minutes following exposure. The feeding (parasitic) stage of the parasite within the skin and gill is called a trophont. The parasitic stage lasts from three days to several months depending on the water temperature (optimum is 21°–23° C.). Under optimum conditions, detachment occurs by three to five days. After a mature parasite leaves the host, it swims to an available surface to begin encystment and reproduction. Parasites that do not encyst within six hours of detachment will not develop infective progeny. Infective theronts develop from trophonts in 10–12 hours, bore through the cyst wall and are infective for 20–96 hours. They die within 96 hours if a suitable host is not available. Under optimum conditions of temperature, water quality, etc., fish will begin to die within fifteen days post-infection.

Similar to the *Edwardsiella ictaluri* model, catfish are pretreated with vanadate, or vanadate is added to the tanks two hours post-infection. This ensures that the parasite has had ample time to infect the host prior to addition of vanadate. The target cell and tissue in this disease is NCC and peripheral blood, respectively. Histopathological assessment comprises the determination of changes in PBL (peripheral blood leukocytes) counts. NCC responses and cytotoxicity assay are evaluated as consequence of the interaction between vanadate treatment and Ich infection.

Evaluation of data from Ich testing is quite straightforward because NCC bind to and probably directly lyse Ich. Assessment of the effects of vanadate thus consist of finding increased numbers of Ich in the PBL and finding increased cytolytic activity of NCC.

Treatment and control of Ich is directed, for example, towards preventing reinfection of fish by free-swimming trophonts. Vanadate offers a completely new and unique approach to control this disease, e.g., modulation of a cytolytic effector (NCC) function. Similar to *Edwardsiella ictaluri* survivors, catfish which survive Ich infections are relatively immune to subsequent Ich infections. Vanadate produces large populations of survivors (that would have otherwise died without treatment); these fish are essentially vaccinated without ever having received a vaccine or bacterin.

The Ich model is amenable to the testing of vanadate-mimetic protein phosphatase inhibitors as therapeutic and/or prophylactic agents against Ich in different fresh water fish in both the domestic and the commercial production markets.

EXAMPLE 8

DEVELOPMENT OF IMMUNITY IN FISH UPON TREATMENT WITH ORTHOVANADATE OR A VANADATE-MIMETIC PROTEIN PHOSPHATASE INHIBITOR

One of the most important sequelae of vanadate or a vanadate-mimetic protein phosphatase inhibitor induced resistance to acute disease from a microorganismic pathogen is that these fish acquire the ability to specifically resist secondary and subsequent insults by this pathogen. Although this is not a prerequisite for establishing the importance of protein phosphatase treatment, there is a significant possibility that, concomitant with the NCC exacerbation of the local intestinal immune responses, survivors develop anti-microorganismic primary antibody responses. This development has important influences on the rationale for the development of vaccines.

The following protocol is used to test firstly the development of immunity in catfish which survived infection with *Edwardsiella ictaluri* and treatment with sodium vanadate. These survivors are reexposed to $LD_{50}$ dosages of *Edwardsiella ictaluri* and survival rates are determined and compared to naive, nonvanadate treated catfish.

Secondly, the antigenicity of survivors and reexposed fish is determined. Edwardsiella ictaluri are highly antigenic [Austin et al. (1987) In: *Bacterial Fish Pathogens, Disease in Farmed and Wild Fish*, Ellis Horwood Limited, John Wiley and Sons, New York, p. 199]. Agglutinin titers are determined in control, first-infection survivors and secondarily challenged survivors. Primary and secondary anti-Edwardsiella antibody (agglutinin) responses are used to access acquired immunity.

These protocols are routine, easy to carry out and straightforward. Immune (resistant) fish are generated in each of the infection/treatment protocols. An increased percentage of survivors are observed in the fish reexposed to microorganismic pathogens. This protocol is amenable to testing with different fish, e.g., different fresh water fish that are produced in large numbers. This protocol is also amenable to testing for the development of immunity to different microorganismic pathogens, e.g., bacterial and protozoan pathogens harmful to commercially produced fish and commercially costly to the fish industry.

EXAMPLE 9

PERSISTENCE OF VANADATE OR A VANADATE-MIMETIC PROTEIN PHOSPHATASE INHIBITOR DURING AND AFTER TREATMENT WITH VANADATE

The chemical half-life of orthovanadate or a vanadate-mimetic protein phosphatase inhibitor is determined by putting identical concentrations of a protein phosphatase inhibitor (e.g., 50 µM) in different 10 gallon fish tanks. At different timed intervals consisting of, for example, 0, 6, 12, 24, 48 and 96 hours following addition of inhibitor to the tanks, fish are placed in each of these different tanks for 48 hours prior to infection with a pathogen, e.g., *Edwardsiella ictaluri*. Each set of fish is incubated with each timed interval group for the same amount of time (e.g., 48 hours) prior to infection. The mortality in each tank is determined. If the fish in the long-duration tanks (e.g., 24–96 hour groups) have higher mortality than in the short-duration tanks (e.g., 0–6 hours groups), it is suggested that the protein phosphatase inhibitor is inactivated in tank water.

The biological half-life of sodium orthovanadate or a vanadate protein phosphatase inhibitor is also determined. Different 10 gallon tanks are prepared so that fish in each tank are pretreated with, for example, sodium orthovanadate (e.g., 50 µM). Each tank receives a complete water change except the "O time" tank. Fish in the "O time" tank are infected with a microorganismic pathogen, e.g., *Edwardsiella ictaluri*. At 6 hours, 12 hours, 24 hours, 48 hours and 96 hours post-treatment with the orthovanadate, fish in each respective tank are infected with the Edwardsiella. Fish are then monitored for morbidity and mortality. This experiment determines whether the protective effect of vanadate or a vanadate-mimetic protein phosphatase inhibitor persists or diminishes with time between inhibitor treatment and infectious challenge. Additionally, this experiment determines whether there is a requirement for the continuous presence of vanadate or a vanadate-mimetic protein phosphatase inhibitor in the tank water in order to elicit a protective response.

Residual levels of vanadate in tissues of orthovanadate treated fish are also determined. Fish that survive the vanadate resistance-inducing protocol are sacrificed at weekly intervals (for the first four weeks) and tissues are harvested and processed for vanadate residue determinations. After the first four weekly sampling times, survivors are monitored for vanadate residues at monthly intervals for at least one year.

EXAMPLE 10

RESIDUAL VANADATE IN FISH TISSUE AFTER VANADATE TREATMENT

The following protocols are designed to determine the effects of vanadate treatment on different fish tissue. Because both the bacterial and protozoan diseases run their courses by two weeks post-infection, it is feasible to monitor NCC activity daily during this time period. Uninfected fish are treated with vanadate for different periods of time and samples are taken for analysis daily.

a. The levels of NCC in various lymphoreticular tissue as a variable of vanadate treatment are determined. Single cell suspensions are prepared from the following fish tissue: PBL, spleen, thymus, liver, anterior kidney and trunk kidney. Absolute numbers of NCC will be determined by flow cytometric analysis with mab 5C6.

b. NCC cytotoxicity is measured as a variable of vanadate treatment and time. Cytotoxicity assays are carried out with IM-9 target cells.

c. The affinity and recycling capacity of NCC are measured. For these experiments chromium$^{51}$ release assays are combined with conjugate assays [Graves et al. (1985) supra] to determine killing capacity ($V_{max}$) and affinity ($K_m$). This is accomplished by transformation of data into a Lineweaver-Burk plot.

d. Histological changes in lymphoreticular tissue are measured following vanadate treatment. At each sampling time for cytotoxicity determination, e.g., flow cytometry, etc., tissue will be taken for histological evaluation. These tissue will consist of anterior kidney, brain, spleen, liver, trunk kidney and thymus.

These protocols are routinely carried out by laboratories in this field and do not require any novel technology.

EXAMPLE 11

HISTOLOGICAL EFFECTS OF IN VIVO ORTHOVANADATE OR VANADATE-MIMETIC PROTEIN PHOSPHATASE INHIBITOR TREATMENT OF FISH

The histological effects of in vivo treatment of fish with sodium orthovanadate, a protein phosphatase inhibitor, or a vanadate-mimetic protein phosphatase inhibitor are evaluated using the following protocols.

Four different treatment groups are evaluated for histological changes: Group 1, control noninfected/ noninhibitor treated; Group 2, pathogen (e.g., *Edwardsiella ictaluri*) infected/noninhibitor treated; Group 3, pathogen infected/ inhibitor treated at optimum protective concentration; Group 4, pathogen infected/inhibitor treated at high, immunosuppressive concentration; and Group 5, inhibitor treated, noninfected. Group 3 fish allow identification of the tissue/ cellular changes which occur concomitant with altered immune responses. Group 4 fish are comparable to tissue ablation experiments that allow observations when a natural effector function is suppressed or removed.

Intestine is harvested daily or weekly from each of the above groups. Tissue is fixed, sectioned, stained (H & E) and examined. The cellular composition is identified by light microscopy and by immunoperoxidase staining. Immunological identification of NCC is facilitated with mab 5C6 [Evans et al. (1988) supra]. The time course of the histological change which occurs in each of the above groups is determined simultaneously with immunological determinations. Because NCC is specifically identified with immunoperoxidase staining in tissue sections, correlations are made for each histological change with NCC cytotoxicity assays. Immune function is determined at each tissue sampling time. NCC is harvested from the tissue used for cytotoxicity assays using known procedures [Chai et al. (1988) *Immunol.* 63:111; Croitoru et al. (1990) *Immunol.* 71:196; Pang et al. (1993) *Immunol.* 79:498]. Thus, histopathological changes are measured concomitant with NCC numbers and the NCC cytolytic functions are evaluated simultaneously.

As an adjunct to the microscopic examination of tissue changes, transmission electron microscopic examinations are carried out on tissue to determine the extent of phagocytosis.

EXAMPLE 12

A KIT COMPRISING A PHARMACEUTICAL COMPOSITION FOR THE TREATMENT OF FISH AGAINST INFECTION CAUSED BY A MICROORGANISMIC PATHOGEN

A pharmaceutical composition for the protection of teleost fish from microorganismic pathogens is prepared to comprise sodium orthovanadate or a vanadate-mimetic protein phosphatase inhibitor and a carrier and/or stabilizer acceptable to fish. For the commercialization and marketing of the vanadate or vanadate-mimetic protein phosphatase inhibitor-containing pharmaceutical composition a kit is prepared. The kit, or alternatively, the pharmaceutical composition may further comprise additional medicaments, for example, an antibiotic such as tetracycline, ampicillin, penicillin, erythromycin, etc.; a fungicide such as sulfamethazine, sulfathiozole, sulfadiazine, sulfamerazine, etc., an antiviral compound such as an oligonucleotide, a phosphothioate, etc.; an anti-inflammatory agent such as naprosyn, motrin, voltaren, etc., and a protein phosphatase inhibitor.

The pharmaceutical composition is present in liquid or solid form, for example, as a solution, tablet, grains, flakes, powder, cube, capsule, or other forms known in the art, such that it is easily dispensable, for example, with an eye dropper, vial, cup, or the like, which is included in the kit. A measurable or a premeasured amount is deliverable to a given amount of aqueous medium (e.g., water) in a contained environment, e.g., aquarium, tank, pond, pool, etc., to give a final concentration of vanadate or vanadate-mimetic protein phosphatase inhibitor that is a therapeutic concentration or a prophylactic concentration in the treatment of fish against a microorganismic pathogen.

Guidelines or directions for use of the pharmaceutical composition may be included in the kit. The dosage of the pharmaceutical composition may be specified, based on, for example, the volume of water, the number of fish, the type of fish, the size of fish, the state of the fish (stressed, normal, infected, etc.) in the contained environment and the type of microorganismic pathogen involved. Directives for the frequency and duration of the treatment as well as instructions for changing the water during a treatment schedule may also be enclosed in the kit.

TABLE 1

Effects of H-7 on NCC Lysis of IM-9 Target Cells

| Inhibitor concentration | Treatment time | Percentage inhibition |
| --- | --- | --- |
| 30 μM | 60 min[a] | 12.5 |
|  | 120 min | 31.0 |
|  | 180 min | 37.8 |
|  | 180 min/wash[b] | 34.2 |
| 60 μM | 60 min | 10.2 |
|  | 120 min | 12.6 |
|  | 180 min | 35.7 |
|  | 180 min/wash | 34.5 |

Note: NCC were incubated with different concentrations of H-7 for 1–3 hours. The inhibitor either remained in the assay or the NCC were washed prior to addition of the chromium-labeled targets. Cytotoxicity assays were for 6 hours (25° C.).
[a]Time of inhibitor treatment prior to adding the target cells. Effector to target cell ratio (E:T ratio) = 80:1. Media control (i.e., percentage specific release) = 25.9%.
[b]NCC were treated for 3 hours and the inhibitor was removed prior to the addition of the target cells.

TABLE 2

Effects of H-8 on NCC Activity

| Inhibitor concentration (μM) | Percentage inhibition |
| --- | --- |
| 30 | 0 |
| 60 | 13.8 |
| 150 | 36.9 |
| 300 | 46.5 |

Note: NCC were treated for 90 minutes at each inhibitor concentration, washed, and added to IM-9 target cells. Supernatants were harvested following a 4-hour assay. Percentage specific release of control cultures was 55.1% (E:T ratio = 80.1).

TABLE 3

Effects of HA1004 on NCC Activity

| Inhibitor concentration[a] | Treatment time | Percentage specific release | Percentage increase[b] |
| --- | --- | --- | --- |
| 30 μM | 60 min | 38.7 | 49.2 |
|  | 120 min | 39.0 | 50.2 |
|  | 180 min | 35.9 | 38.5 |
|  | 180 min/wash | 36.0 | 38.7 |
| 60 μM | 60 min | 38.5 | 48.3 |
|  | 120 min | 36.9 | 42.1 |
|  | 180 min | 36.5 | 40.6 |
|  | 180 min/wash | 34.2 | 31.8 |

[a]NCC were treated with different concentrations of the inhibitor HA1004. Target cells (IM-9) were added without removal of the inhibitor except in the "180 minutes/wash" experiment. The cytotoxicity assay was for 6 hours at 25° C.
[b]Percentage increase calculations were based on comparisons with the media control which had a 25.9% specific release.

TABLE 4

Effects of Genistein on NCC Lysis of IM-9 Target Cells

| Genistein concentration | Percentage inhibition |
| --- | --- |
| 14.2[a] | 55.5[b] |
| 28.4 | 75.9 |
| 57.0 | 64.9 |
| 142.0 | 94.0 |

Note: NCC were treated with different concentrations of genistein. Chromium-labeled IM-9 target cells were added (at an E:T ratio of 20:1) and the cells were cultured for 6 hours at 25° C. The supernatants were then harvested and counted for radioactivity.
[a]Concentrations given in μg/ml (100 μl present in each microwell).
[b]Percentage inhibition calculated based on 19.1% specific release in media controls.

TABLE 5

Effects of A23187 Costimulus on the Cytotoxicity of NCC Following Treatment with Protein Kinase Inhibitors

| Treatment[a] | Percentage specific release[b] |
| --- | --- |
| Media control | 20.6 |
| A23187 | 81.0 |
| H-7 | 9.1 |
| H-7 - A23187 | 80.9 |
| HA1004 | 33.2 |
| HA1004 - A23187 | 82.4 |
| Genistein | 11.0 |
| Genistein - A23187 | 81.5 |
| Mab 5C6 | 30.5 |
| Mab 5C6 - A23187 | 84.4 |

[a]Concentrations used were $10^{-4}$M A23187; 60 μM H-7 and HA1004; 0.5 μg/ml genistein; and 1:3 dilution of tissue culture supernatant.
[b]E:T ratio = 40:1.

TABLE 6

Effects of Protein Kinase Inhibitors on mab 5C6-Activated NCC

| Treatment | Percentage of control (E:T ratio) | |
| --- | --- | --- |
|  | 40%[a] | 20% |
| Isotype control (IC)[b] | 125.9 | 122.3 |
| Mab 5C6 | 152.4 | 264.4 |
| H-7[c] | 37.5 | 53.9 |
| IC + H-7 | 27.7 | 29.3 |
| Mab 5C6 + H-7 | 93.2 | 0.1 |
| HA1004[c] | 210.6 | 243.4 |

TABLE 6-continued

Effects of Protein Kinase Inhibitors on mab 5C6-Activated NCC

| Treatment | Percentage of control (E:T ratio) | |
|---|---|---|
| | 40%[a] | 20% |
| IC + HA1004 | 161.2 | 221.6 |
| Mab 5C6 + HA1004 | 191.3 | 379.9 |
| Genistein[d] | 38.9 | 35.5 |
| IC + Genistein | 37.4 | 32.6 |
| Mab 5C6 + Genistein | 40.3 | 32.9 |

[a] $4 \times 10^6$ NCC/ml.
[b] Ammonium sulfate precipitated mabs 5C6 and TGE (1:50 dilution).
[c] 60 μM concentration.
[d] 0.5 μg/ml.

TABLE 7

Effects of Phosphatase Inhibitors on NCC Cytotoxic Activity

| Inhibitor | Concentration (mM) | Percentage of control[a] | | |
|---|---|---|---|---|
| | | 100:1 | 50:1 | 25:1 |
| Lithium chloride | 5 | 97.2 | 88.9 | 98.4 |
| | 10 | 99.0 | 107.4 | 105.1 |
| | 20 | 103.8 | 118.9 | 190.1 |
| Sodium fluoride | 5 | 123.2 | 136.9 | 210.3 |
| | 10 | 153.7 | 183.9 | 333.3 |
| | 20 | 157.3 | 225.8 | 635.3 |
| Sodium vanadate | 2.5 | 148.6 | 155.3 | 494.4 |
| | 5 | 162.1 | 212.4 | 664.4 |
| | 10 | 159.1 | 225.8 | 897.1 |

Note: NCC were treated for 120 minutes with different concentrations of inhibitors. IM-9 target cells were added and the cytotoxicity assay was carried out for 4 hours.
[a] Calculations based on values obtained for specific release (SR) in the presence of media. At (E:T) = 100:1, SR = 39.1%; at E:T = 50:1, SR = 21.7%; at E:T = 25:1, SR = 4.47%.

TABLE 8

Effects of Protein Phosphatase Inhibitors on NCC Lysis of IM-9 Target Cells

| Treatment | Concentration (mM) | Percent Specific Release (E:T Ratio) | | |
|---|---|---|---|---|
| | | 10 | 50 | 25 |
| Media | — | 39 | 21 | 4 |
| LiCl | 5 | 38 | 19 | 4 |
| | 10 | 38 | 23 | 4 |
| | 20 | 40 | 25 | 8 |
| NaF | 5 | 48 | 29 | 9 |
| | 10 | 60 | 39 | 14 |
| | 20 | 61 | 49 | 28 |
| Na$_3$VO$_4$ | 2.5 | 58 | 33 | 22 |
| | 5 | 63 | 46 | 29 |
| | 10 | 62 | 49 | 40 |

TABLE 9

Effects of Phosphatase Inhibitors on NCC Activity from Stressed Fish

| Group | Treatment | | Percent Specific Release* |
|---|---|---|---|
| | NaF (mM) | Na$_3$VO$_4$ (mM) | |
| Control | — | — | 0.9 |
| I | 5 | — | 1.4 |

TABLE 9-continued

Effects of Phosphatase Inhibitors on NCC Activity from Stressed Fish

| Group | Treatment | | Percent Specific Release* |
|---|---|---|---|
| | NaF (mM) | Na$_3$VO$_4$ (mM) | |
| | 10 | — | 4.4 |
| | 20 | — | 22.0 |
| II | — | 2.5 | 7.3 |
| | — | 5.0 | 9.9 |
| | — | 10.0 | 13.1 |
| III | 5 | 2.5 | 14.0 |
| | 10 | 2.5 | 22.5 |
| | 20 | 2.5 | 36.1 |
| IV | 5 | 5.0 | 16.4 |
| | 10 | 5.0 | 22.6 |
| | 20 | 5.0 | 27.4 |
| V | 5 | 10.0 | 20.1 |
| | 10 | 10.0 | 17.1 |
| | 20 | 10.0 | 20.1 |

*100:1 effector target cell ratio. Four-hour cytotoxicity assay.

TABLE 10

Effects of In Vivo Vanadate Treatment on the NCC Content of Anterior Kidney Tissue

| Hours Post-Treatment | Control (% NCC) | Treatment | |
|---|---|---|---|
| | | 50 μM (% NCC) | 125 μM (% NCC) |
| 3 | 60 (3.2)[1] | 51 (3.1)[1] | 53 (6.5)[1] |
| 24 | 55 (2.6) | 60 (2.8) | 52 (3.2) |
| 48 | 52 (2.1) | 66 (3.5) | 73 (2.7) |
| 72 | 70 (2.3) | 72 (3.1) | 61 (1.9) |
| 96 | 61 (3.6) | 78 (1.6) | — |

[1] Total cells/ml × $10^0$

We claim:

1. A method for the therapeutic or prophylactic treatment of a teleost fish against infection caused by a microorganismic pathogen comprising the step of providing in soluble form into an aquatic environment administering a therapeutically or prophylactically effective concentration of an orthovanadate salt such that said infected fish is protected against the development or progression of an infection or disease associated with said pathogen.

2. The method according to claim 1 wherein said therapeutic or prophylactic treatment is the therapeutic treatment and said therapeutically or prophylactically effective concentration is a therapeutically effective concentration.

3. The method according to claim 1 wherein said therapeutic or prophylactic treatment is the prophylactic treatment and said therapeutically or prophylactically effective concentration is a prophylactically effective concentration.

4. The method according to claim 1 wherein said orthovanadate salt is sodium orthovanadate.

5. The method according to claim 1 wherein said teleost fish is a commercially produced fish.

6. The method according to claim 1 wherein said teleost fish is a catfish.

7. The method according to claim 1 wherein said teleost fish is a domestic fish.

8. The method according to claim 1 wherein said microorganismic pathogen is selected from the group consisting of a bacterium, a protozoan, a virus, a fungus and a parasite.

9. The method according to claim 1 wherein said microorganismic pathogen is a bacterium or a protozoan.

10. The method according to claim 9 wherein said microorganismic pathogen is an Edwardsiella.

11. The method according to claim 9 wherein said microorganismic pathogen is *Ichthyophthirius multifiliis*.

12. The method according to claim 4 wherein said orthovanadate salt is administered in conjunction with a medicament selected from the group consisting of an antibiotic, a protein phosphatase inhibitor, a fungicide, an antiviral compound, and an anti-inflammatory agent.

13. The method according to claim 2 wherein said teleost fish is a catfish, said microorganismic pathogen is *Edwardsiella ictaluri*, said orthovanadate salt is sodium orthovanadate, and said therapeutically effective concentration is between approximately 10 μM and approximately 25 μM.

14. The method according to claim 3 wherein said teleost fish is a catfish, said microorganismic pathogen is *Edwardsiella ictaluri*, said orthovanadate salt is sodium orthovanadate, and said prophylactically effective concentration is between approximately 5 μM and approximately 50 μM.

15. A method of developing resistance against an infection or disease caused by a microorganismic pathogen comprising the step of exposing a teleost fish infected with said microorganismic pathogen to a therapeutically effective concentration of an orthovanadate salt such that said fish does not develop said infection or disease upon a subsequent exposure to said microorganismic pathogen.

16. A pharmaceutical composition soluble and externally administrable into an aquatic environment, for the therapeutic or prophylactic treatment of a teleost fish against infection caused by a microorganismic pathogen to which said fish is susceptible comprising an orthovanadate salt, and a medicament selected from the group consisting of an antibiotic, a protein phosphatase inhibitor, a fungicide, an antiviral compound and an anti-inflammatory agent and a pharmaceutical carrier acceptable to said fish.

17. The pharmaceutical composition according to claim 16 further comprising a medicament selected from the group consisting of an antibiotic, a protein phosphatase inhibitor, a fungicide, and antiviral compound and an anti-inflammatory agent.

18. A kit comprising a pharmaceutical composition and a means for dispensing said pharmaceutical composition for the therapeutic or prophylactic treatment of a teleost fish housed in a contained aquatic environment against infection caused by a microorganismic pathogen, comprising an orthovanadate salt, and a medicament selected from the group consisting of an antibiotic, a protein phosphatase inhibitor, a fungicide, an antiviral compound and an anti-inflammatory agent and a pharmaceutical carrier, acceptable to said fish, in a dispensable form such that a measurable or premeasured amount can be delivered to said contained aquatic environment to give a therapeutically effective concentration or a prophylactically effective concentration of said orthovanadate salt.

\* \* \* \* \*